United States Patent [19]

Birch et al.

[11] Patent Number: 5,935,973
[45] Date of Patent: Aug. 10, 1999

[54] HETEROCYCLCARBOXAMIDE DERIVATIVES AND THEIR USE AS THERAPEUTIC AGENTS

[75] Inventors: Alan Martin Birch; David John Heal; Frank Kerrigan; Keith Frank Martin; Patricia Lesley Needham; Bruce Jeremy Sargent, all of Nottingham, United Kingdom

[73] Assignee: Knoll Aktiengesellschaft, Ludwigshafen, Germany

[21] Appl. No.: 08/981,671

[22] PCT Filed: Jul. 2, 1996

[86] PCT No.: PCT/EP96/02890

§ 371 Date: Jan. 5, 1998

§ 102(e) Date: Jan. 5, 1998

[87] PCT Pub. No.: WO97/03071

PCT Pub. Date: Jan. 30, 1997

[30] Foreign Application Priority Data

Jul. 13, 1995 [GB] United Kingdom .................. 9514380

[51] Int. Cl.$^6$ ...................... A61K 31/335; C07D 319/20; C07D 207/04; C07D 207/50; C07D 211/06; C07D 211/98

[52] U.S. Cl. .......................... 514/321; 514/183; 514/256; 514/259; 514/260; 514/272; 514/274; 514/312; 514/313; 514/314; 514/316; 514/318; 514/319; 514/320; 514/365; 514/369; 514/370; 514/372; 514/374; 514/376; 514/377; 514/378; 514/380; 514/381; 514/382; 514/383; 514/384; 514/406; 514/407; 514/422; 544/283; 544/286; 544/287; 544/288; 544/292; 544/293; 544/311; 544/316; 544/319; 544/320; 544/321; 544/322; 544/323; 544/329; 544/332; 544/335; 546/155; 546/156; 546/159; 546/168; 546/187; 546/189; 546/190; 546/193; 546/194; 546/195; 546/196; 546/197; 546/205; 546/206; 546/276.4; 546/279.1; 548/182; 548/183; 548/184; 548/185; 548/188; 548/190; 548/191; 548/192; 548/194; 548/200; 548/206; 548/225; 548/226; 548/227; 548/228; 548/230; 548/233; 548/236; 548/240; 548/243; 548/244; 548/245; 548/246; 548/248; 548/253; 548/255; 548/263.2; 548/264.4; 548/265.4; 548/265.6; 548/266.8; 548/517; 548/525; 548/526; 548/527

[58] Field of Search ..................... 514/183, 256, 514/259, 260, 272, 274, 312, 313, 314, 316, 318, 319, 320, 321, 365, 369, 370, 372, 374, 376, 377, 378, 380, 381, 382, 383, 384, 406, 407, 422; 544/283, 286, 287, 288, 292, 293, 311, 316, 319, 320, 321, 322, 323, 329, 332, 335; 546/155, 156, 159, 168, 187, 189, 190, 193, 194, 195, 196, 197, 205, 206, 276.4, 279.1; 548/182, 183, 184, 185, 188, 190, 191, 192, 194, 200, 206, 225, 226, 227, 228, 230, 233, 236, 240, 243, 244, 245, 246, 248, 253, 255, 263.2, 264.4, 265.4, 265.6, 266.8, 517, 525, 526, 527

[56] References Cited

U.S. PATENT DOCUMENTS 5,314,895  5/1994  Desai et al. ............................ 514/318

FOREIGN PATENT DOCUMENTS 2724383  3/1996  France .
91/13872  9/1991  WIPO .
95/02592  1/1995  WIPO .
95/07274  3/1995  WIPO .

OTHER PUBLICATIONS

Giardina et al., *J. Med. Chem.*, vol. 28, No. 9, 1985, pp. 1354–1357.

Ennis et al., *J. Med. Chem.*, vol. 35, No. 16, 1992, pp. 3058–3066.

Primary Examiner—Mukund J. Shah
Assistant Examiner—Brenda Coleman
Attorney, Agent, or Firm—Keil & Weinkauf

[57] ABSTRACT

Compounds of formula I

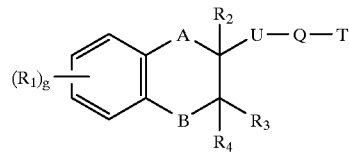

and pharmaceutically acceptable salts thereof in which A is methylene or O; B is methylene or O; g is 0,1,2,3 or 4; $R_1$ is an optional substituent; U is an alkylene chain optionally substituted by one or more alkyl; Q represents a divalent group containing nitrogen atoms; and T represents CO.HET, have utility in the treatment of central nervous system disorders, for example depression, anxiety, psychoses (for example schizophrenia), tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behavior, panic attacks, social phobias, eating disorders and anorexia, cardiovascular and cerebrovascular disorders, non-insulin dependent diabetes mellitus, hyperglycaemia, constipation, arrhythmia, disorders of the neuroendocrine system, stress, prostatic hypertrophy, and spasticity.

11 Claims, No Drawings

HETEROCYCLCARBOXAMIDE DERIVATIVES AND THEIR USE AS THERAPEUTIC AGENTS

This application is a 371 of PCT/EP96/02890, filed on Jul. 2, 1996.

The present invention relates to novel heteroarylcarboxamide compounds which have affinity for 5-HT$_{1A}$ and/or $\alpha_1$ and/or $\alpha_2$ and/or D$_2$ receptors, to processes for their preparation, to pharmaceutical compositions containing them and to their use in the treatment of central nervous system disorders, for example depression, anxiety, psychoses (for example schizophrenia), tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behaviour, panic attacks, social phobias, eating disorders and anorexia, cardiovascular and cerebrovascular disorders, non-insulin dependent diabetes mellitus, hyperglycaemia, constipation, arrhythmia, disorders of the neuroendocrine system, stress, prostatic hypertrophy, and spasticity.

The present invention provides compounds of formula I

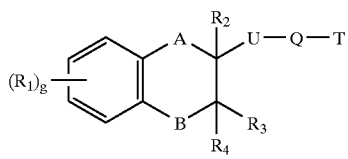

including pharmaceutically acceptable salts thereof in which

A is methylene or O;

B is methylene or O;

g is 0, 1, 2, 3 or 4;

R$_1$ represents a) halo; b) an alkyl group containing 1 to 3 carbon atoms optionally substituted by one or more halo; c) an alkoxy group containing 1 to 3 carbon atoms optionally substituted by one or more halo; d) an alkylthio group containing 1 to 3 carbon atoms optionally substituted by one or more halo; e) hydroxy; f) an acyloxy group containing 1 to 3 carbon atoms; g) hydroxymethyl: h) cyano; i) an alkanoyl group containing 1 to 6 carbon atoms; j) an alkoxycarbonyl group containing 2 to 6 carbon atoms; k) a carbamoyl group or carbamoylmethyl group each optionally N-substituted by one or two alkyl groups each containing 1 to 3 carbon atoms; l) a sulphamoyl or sulphamoylmethyl group each optionally N-substituted by one or two alkyl groups each containing 1 to 3 carbon atoms; m) an alkylsulphonyloxy group containing 1 to 3 carbon atoms optionally substituted by one or more halo; n) a furyl group; o) an amino group optionally substituted by one or two alkyl groups each containing 1 to 3 carbon atoms; or two adjacent R$_1$ groups together with the carbon atoms to which they are attached form a fused benz ring, the substituents represented by R$_1$ being the same or different when g is 2, 3 or 4;

R$_2$ is H, an alkyl group containing 1 to 3 carbon atoms optionally substituted by one or more halo, or an alkoxy group containing 1 to 3 carbon atoms optionally substituted by one or more halo;

R$_3$ and R$_4$, which are the same or different, are H, or an alkyl group containing 1 to 3 carbon atoms optionally substituted by one or more halo;

U is an alkylene chain containing 1 to 3 carbon atoms, optionally substituted by one or more alkyl groups each containing 1 to 3 carbon atoms;

Q represents a divalent group of formula IIa, IIb or IIc

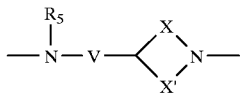

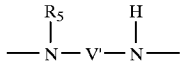

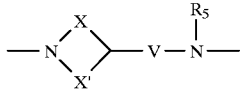

in which V is a bond or an alkylene chain containing 1 to 3 carbon atoms optionally substituted by one or more alkyl groups each containing 1 to 3 carbon atoms;

V' is an alkylene chain containing 2 to 6 carbon atoms, optionally substituted by one or more alkyl groups each containing 1 to 3 carbon atoms;

X is an alkylene chain containing 0 to 2 carbon atoms and X' is an alkylene chain containing 1 to 4 carbon atoms provided that the total number of carbon atoms in X and X' amounts to 3 or 4; R$_5$ is H or an alkyl group containing 1 to 3 carbon atoms; and T represents the group CO.HET in which HET is 2-, 3- or 4-pyridyl, 2-, 4- or 5-pyrimidinyl, 2- or 3-thienyl, 2- or 3-furyl, 2-, 3- or 7-benzo[b]furanyl, 2,3-dihydro-7-benzo[b]furanyl, 2-, 3- or 7-benzo[b]thienyl, 2-, 3- or 4-piperidyl, 3-, 4- or 5-pyrazolyl, 4- or 5-triazolyl, 5-tetrazolyl, 2-, 3-, 4-, or 8-quinolinyl, 2- or 4-quinazolinyl, 3-, 4- or 5-isoxazolyl, 2-, 4- or 5-oxazolyl, 3-, 4- or 5-isothiazolyl or 2-, 4- or 5-thiazolyl each of which may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group containing 1 to 3 carbon atoms optionally substituted by one or more halo, e) hydroxy, f) an acyloxy group containing 1 to 3 carbon atoms, g) hydroxymethyl, h) cyano, i) an alkanoyl group containing 1 to 6 carbon atoms, j) an alkoxycarbonyl group containing 2 to 6 carbon atoms, k) a carbamoyl group or carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, m) an amino group optionally substituted by one or two alkyl groups each containing 1 to 5 carbon atoms, n) 1-pyrrolyl or o) 1-pyrrolidinyl or piperidino.

In preferred compounds of formula I, A is O.

In preferred compounds of formula I, B is O.

In more preferred compounds of formula I, both A and B are O.

In preferred compounds of formula I, g is 0, 1 or 2.

In preferred compounds of formula I, in which g is 1 or 2, R$_1$ represents halo (for example fluoro, chloro, or bromo), an alkyl group containing 1 to 3 carbon atoms optionally substituted by one or more halo, an alkoxy group containing 1 to 3 carbon atoms, an alkanesulphonyloxy group containing 1 to 3 carbon atoms optionally substituted by one or more halo, or hydroxy. In more preferred compounds of formula I, in which g is 1 or 2, R$_1$ represents bromo, chloro, fluoro, trifluoromethyl, trifluoromethanesulphonyloxy, methyl or methoxy.

In preferred compounds of formula I, $R_2$ is H or an alkyl group containing 1 to 3 carbon atoms. In more preferred compounds of formula I, $R_2$ is H.

In preferred compounds of formula I, $R_3$ and $R_4$, which are the same or different, are H or methyl. In more preferred compounds of formula I, $R_3$ and $R_4$ are both H.

In preferred compounds of formula I, U is methylene.

In preferred compounds of formula I in which Q is a group of formula IIa or IIc, V is methylene or ethylene, and X and X' are both ethylene.

In preferred compounds of formula I, in which Q is a group of formula IIb, V' is an alkylene chain containing 2 to 4 carbon atoms.

In more preferred compounds of formula I, Q is a group of formula IIa or IIc and V is methylene.

In preferred compounds of formula I, $R_5$ is H or methyl. In more preferred compounds of formula I, $R_5$ is H.

In preferred compounds of formula I, HET is 2-, 3- or 4-pyridyl, 8-quinolinyl, or 2-thienyl each optionally substituted by one or more substituents selected from methyl, methoxy, trifluoromethyl, halo, methylthio, 1-pyrrolyl, or an amino group optionally substitued by one or two alkyl groups each containing 1 to 3 carbon atoms. In more preferred compounds of formula I, HET is 2-pyridyl, 3-pyridyl, 8-quinolinyl, or 2-thienyl each optionally substituted by an amino group, methyl, methoxy, 1-pyrrolyl, trifluoromethyl, methylthio or bromo. In most preferred compounds of formula I HET is 2-pyridyl, or 3-pyridyl optionally substituted by an amino group.

In preferred compounds of formula I, A and B are both O; g is 0, 1 or 2; $R_1$ represents halo (for example fluoro, chloro, or bromo), an alkyl group containing 1 to 3 carbon atoms optionally substituted by one or more halo, an alkoxy group containing 1 to 3 carbon atoms, an alkylsulphonyloxy group containing 1 to 3 carbon atoms optionally substituted by one or more halo, or hydroxy; $R_2$ is H or an alkyl group containing 1 to 3 carbon atoms; $R_3$ and $R_4$, which are the same or different, are H or methyl; U is methylene; Q is a group of formula IIa or IIc; V is methylene; $R_5$ is H or methyl; X and X' are both ethylene; and HET is 2-, 3- or 4-pyridyl, 8-quinolinyl, or 2-thienyl each optionally substituted by one or more substituents selected from methyl, methoxy, trifluoromethyl, halo, methylthio, 1-pyrrolyl, or an amino group optionally substitued by one or two alkyl groups each containing 1 to 3 carbon atoms.

It will be understood that any group mentioned herein which contains a chain of three or more atoms signifies a group in which the chain may be straight or branched. For example, an alkyl group may comprise propyl, which includes n-propyl and isopropyl, and butyl, which includes n-butyl, sec-butyl, isobutyl and tert-butyl. The term 'halo' as used herein signifies fluoro, chloro, bromo and iodo.

Compounds of formula I may exist as salts with pharmaceutically acceptable acids. Examples of such salts include hydrochlorides, hydrobromides, sulphates, methanesulphonates, nitrates, maleates, acetates, citrates, fumarates, tartrates [eg (+)-tartrates, (−)-tartrates or mixtures thereof including racemic mixtures], succinates, benzoates and salts with amino acids such as glutamic acid. Compounds of formula I and their salts may exist in the form of solvates (for example hydrates).

Compounds of formula I contain one or more chiral centres, and exist in different optically active forms. When compounds of formula I contain one chiral centre, the compounds exist in two enantiomeric forms and the present invention includes both enantiomers and mixtures of enantiomers. The enantiomers may be resolved by methods known to those skilled in the art, for example by formation of diastereoisomeric salts which may be separated, for example, by crystallisation; formation of diastereoisomeric derivatives or complexes which may be separated, for example, by crystallisation, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesised by asymmetric synthesis using optically active reagents, substrates, catalysts or solvents, or by converting one enantiomer into the other by asymmetric transformation.

When a compound of formula I contains more than one chiral centre it may exist in diastereoisomeric forms. The diastereoisomeric pairs may be separated by methods known to this skilled in the art, for example chromatography or crystallisation and the individual enantiomers within each pair may be separated as described above. The present invention includes each diastereoisomer of compounds of formula I and mixtures thereof.

Certain compounds of formula I and their salts may exist in more than one crystal form and the present invention includes each crystal form and mixtures thereof. Certain compounds of formula I and their salts may also exist in the form of solvates, for example hydrates, and the present invention includes each solvate and mixtures thereof.

Specific compounds of formula I are:

2-Amino-N-{[1-(7-chloro-1,4-benzodioxan-2-ylmethyl)-4-piperidyl]methyl}pyridine-3-carboxamide;

2-Amino-N-{[1-(8-chloro-1,4-benzodioxan-2-ylmethyl)-4-piperidyl]methyl}pyridine-3-carboxamide;

2-Amino-N-{[1-(8-fluoro-1,4-benzodioxan-2-ylmethyl)-4-piperidyl]methyl}pyridine-3-carboxamide;

2-Amino-N-{[1-(1,4-benzodioxan-2-ylmethyl)-4-piperidyl]methyl}pyridine-3-carboxamide;

2-Amino-N-{[1-(7-methyl-1,4-benzodioxan-2-ylmethyl)-4-piperidyl]methyl}pyridine-3-carboxamide;

N-{[1-(1,4-Benzodioxan-2-ylmethyl)-4-piperidyl]methyl}pyridine-2-carboxamide;

2-Amino-N{[1-(7-methoxy-1,4-benzodioxan-2-ylmethyl)-4-piperidyl]methyl}pyridine-3-carboxamide;

N-{[1-(1,4-Benzodioxan-2-ylmethyl)-4-piperidyl]methyl}quinoline-8-carboxamide;

N-{[1-(8-Chloro-1,4-benzodioxan-2-ylmethyl)-4-piperidyl]methyl}-2-methylpyridine-3-carboxamide;

2-Amino-N-{[1-(7-fluoro-1,4-benzodioxan-2-ylmethyl)-4-piperidyl]methyl}pyridine-3-carboxamide;

2-Amino-N-{[1-(8-methoxy-1,4-benzodioxan-2-ylmethyl)-4-piperidyl]methyl}pyridine-3-carboxamide;

N-{[1-(7-Chloro-1,4-benzodioxan-2-ylmethyl)-4-piperidyl]methyl}pyridine-2-carboxamide;

2-Amino-N-{[1-(8-methyl-1,4-benzodioxan-2-ylmethyl)-4-piperidyl]methyl}pyridine-3-carboxamide;

2-Amino-N-{[1-(7-chloro-1,4-benzodioxan-2-ylmethyl)-4-piperidyl]methyl}-6-methylpyridine-3-carboxamide;

3-Amino-N-{[1-(1,4-benzodioxan-2-ylmethyl)-4-piperidyl]methyl}-thiophene-2-carboxamide;

3-Amino-N-{[1-(7-chloro-1,4-benzodioxan-2-ylmethyl)-4-piperidyl]methyl}thiophene-2-carboxamide;

N-{[1-(7-Chloro-1,4-benzodioxan-2-ylmethyl)-4-piperidyl]methyl}-2-methylpyridine-3-carboxamide;

1-(2-Aminonicotinoyl)-4-N-(7-chloro-1,4-benzodioxan-2-ylmethyl)aminomethylpiperidine;
2-Amino-N-{[1-(8-trifluoromethyl-1,4-benzodioxan-2-ylmethyl)-4-piperidyl]methyl}pyridine-3-carboxamide;
2-Amino-N-{[1-(7-bromo-1,4-benzodioxan-2-ylmethyl)-4-piperidyl]methyl}pyridine-3-carboxamide;
N-{[1-(7-Chloro-1,4-benzodioxan-2-ylmethyl)-4-piperidyl]methyl}pyridine-3-carboxamide;
N-{[1-(7-Chloro-1,4-benzodioxan-2-ylmethyl)-4-piperidyl]methyl}quinoline-8-carboxamide;
N-{[1-(8-Chloro-1,4-benzodioxan-2-ylmethyl)-4-piperidyl]methyl}pyridine-3-carboxamide;
N-{[1-(7-Chloro-1,4-benzodioxan-2-ylmethyl)-4-piperidyl]methyl}-6-methylpyridine-2-carboxamide;
N-{[1-(7-Chloro-1,4-benzodioxan-2-ylmethyl)-4-piperidyl]methyl}-2-methoxypyridine-3-carboxamide;
2-Amino-N-{[1-(7,8-difluoro-1,4-benzodioxan-2-ylmethyl)-4-piperidyl]methyl}pyridine-3-carboxamide;
2-Amino-N-{[1-(8-trifluoromethanesulphonyloxy-1,4-benzodioxan-2-ylmethyl)-4-piperidyl]methyl}pyridine-3-carboxamide;
4-[N-(7-Chloro-1,4-benzodioxan-2-ylmethyl)aminomethyl]-1-(2-pyridylcarbonyl)-piperidine;
N{[1-(7-Methyl-1,4-benzodioxan-2-ylmethyl)-4-piperidyl]methyl}pyridine-3-carboxamide;
2-Methyl-N-{[1-(7-methyl-1,4-benzodioxan-2-ylmethyl)-4-piperidyl]methyl}pyridine-3-carboxamide;
N-{[1-(7-Methyl-1,4-benzodioxan-2-ylmethyl)-4-piperidyl]methyl}-6-(1-pyrrolyl)pyridine-3-carboxamide;
N-{[1-(7-Methyl-1,4-benzodioxan-2-ylmethyl)-4-piperidyl]methyl}-2-(methylthio)pyridine-3-carboxamide;
5-Bromo- N{[1-(7-methyl-1,4-benzodioxan-2-ylmethyl)-4-piperidyl]methyl}pyridine-3-carboxamide;
N-{[1-(7-Bromo-1,4-benzodioxan-2-ylmethyl)-4-piperidyl]methyl}pyridine-3-carboxamide;
N-{[1-(7-Bromo-1,4-benzodioxan-2-ylmethyl)-4-piperidyl]methyl}-2-methylpyridine-3-carboxamide;
N-{[1-(7-Bromo-1,4-benzodioxan-2-ylmethyl)-4-piperidyl]methyl}-6-(1-pyrrolyl)pyridine-3-carboxamide;
N-{[1-(7-Bromo-1,4-benzodioxan-2-ylmethyl)-4-piperidyl]methyl}-2-(methylthio)pyridine-3-carboxamide;
5-Bromo-N-{[1-(7-bromo-1,4-benzodioxan-2-ylmethyl)-4-piperidyl]methyl}pyridine-3-carboxamide;
N-{[1-(7-Chloro-1,4-benzodioxan-2-ylmethyl)-4-piperidyl]methyl}-6-(1-pyrrolyl)pyridine-3-carboxamide;
N-{[1-(7-Chloro-1,4-benzodioxan-2-ylmethyl)-4-piperidyl]methyl}-2-(methylthio)pyridine-3-carboxamide;
5-Bromo- N-{[1-(7-chloro-1,4-benzodioxan-2-ylmethyl)-4-piperidyl]methyl}pyridine-3-carboxamide;
N-{[1-(7-Fluoro-1,4-benzodioxan-2-ylmethyl)-4-piperidyl]methyl}pyridine-3-carboxamide;
N-{[1-(7-Fluoro-1,4-benzodioxan-2-ylmethyl)-4-piperidyl]methyl}-2-(methylthio)pyridine-3-carboxamide;
N{[1-(8-Trifluoromethyl-1,4-benzodioxan-2-ylmethyl)-4-piperidyl]methyl}pyridine-3-carboxamide;
2-Methyl-N-{[1-(8-trifluoromethyl-1,4-benzodioxan-2-ylmethyl)-4-piperidyl]methyl}pyridine-3-carboxamide;
6-(1-Pyrrolyl)-N-{[1-(8-trifluoromethyl-1,4-benzodioxan-2-ylmethyl)-4-piperidyl]methyl}pyridine-3-carboxamide;
2-(Methylthio)-N-{[1-(8-trifluoromethyl-1,4-benzodioxan-2-ylmethyl)-4-piperidyl]methyl}pyridine-3-carboxamide;
5-Bromo-N-{[1-(8-trifluoromethyl-1,4-benzodioxan-2-ylmethyl)-4-piperidyl]methyl}pyridine-3-carboxamide;
N-{[1-(8-Chloro-1,4-benzodioxan-2-ylmethyl)-4-piperidyl]methyl}-6-(1-pyrrolyl)pyridine-3-carboxamide;
N-{[1-(8-Chloro-1,4-benzodioxan-2-ylmethyl)-4-piperidyl]methyl}-2-(methylthio)pyridine-3-carboxamide;
5-Bromo-N-{[1-(8-chloro-1,4-benzodioxan-2-ylmethyl)-4-piperidyl]methyl}pyridine-3-carboxamide;
and pharmaceutically acceptable salts thereof in the form of individual enantiomers, racemates, or other mixtures of enantiomers.

Specific enantiomeric forms of compounds of formula I include:
(S)-2-Amino-N-{[1-(7-chloro-1,4-benzodioxan-2-ylmethyl)-4-piperidyl]methyl}- pyridine-3-carboxamide;
(S)-2-Amino-N-{[1-(8-chloro-1,4-benzodioxan-2-ylmethyl)-4-piperidyl]methyl}- pyridine-3-carboxamide;
(S)-2-Amino-N-{[1-(8-fluoro-1,4-benzodioxan-2-ylmethyl)-4-piperidyl]methyl}- pyridine-3-carboxamide;
(S)-2-Amino-N-{[1-(7-methyl-1,4-benzodioxan-2-ylmethyl)-4-piperidyl]methyl}-pyridine-3-carboxamide;
(S)-2-Amino-N-{[1-(7-methoxy-1,4-benzodioxan-2-ylmethyl)-4-piperidyl]methyl}-pyridine-3-carboxamide;
(S)-N-{[1-(8-chloro-1,4-benzodioxan-2-ylmethyl)-4-piperidyl]methyl}-2-methylpyridine-3-carboxamide;
(S)-N-{[1-(7-Chloro-1,4-benzodioxan-2-ylmethyl)-4-piperidyl]methyl}pyridine-2-carboxamide;
(S)-2-Amino-N-{[1-(8-methyl-1,4-benzodioxan-2-ylmethyl)-4-piperidyl]methyl}-pyridine-3-carboxamide;
(S)-2-Amino-N-{[1-(7-chloro-1,4-benzodioxan-2-ylmethyl)-4-piperidyl]methyl}-6-methylpyridine-3-carboxamide;
(S)-2-Amino-N-{[1-(1,4-benzodioxan-2-ylmethyl)-4-piperidyl]methyl}pyridine-3-carboxamide;
(S)-3-Amino-N-{[1-(7-chloro-1,4-benzodioxan-2-ylmethyl)-4-piperidyl]methyl}-thiophene-2-carboxamide;
(S)-N-{[1-(7-chloro-1,4-benzodioxan-2-ylmethyl)-4-piperidyl]methyl}-2-methylpyridine-3-carboxamide;
(S)-2-Amino-N-{[1-(8-trifluoromethyl-1,4-benzodioxan-2-ylmethyl)-4-piperidyl]methyl}- pyridine-3-carboxamide;
(S)-2-Amino-N-{[1-(7-bromo-1,4-benzodioxan-2-ylmethyl)-4-piperidyl]methyl}pyridine-3-carboxamide;
(S)-N-{[1-(7-Chloro-1,4-benzodioxan-2-ylmethyl)-4-piperidyl]methyl}pyridine-3-carboxamide;
(S)-N-{[1-(7-Chloro-1,4-benzodioxan-2-ylmethyl)-4-piperidyl]methyl}quinoline-8-carboxamide;
(S)-N-{[1-(8-Chloro-1,4-benzodioxan-2-ylmethyl)-4-piperidyl]methyl}pyridine-3-carboxamide;
(S)-N-{[1-(7-Chloro-1,4-benzodioxan-2-ylmethyl)-4-piperidyl]methyl}-2-methoxy-pyridine-3-carboxamide;
(S)-2-Amino-N-{[1-(7,8-difluoro-1,4-benzodioxan-2-ylmethyl)-4-piperidyl]methyl}-pyridine-3-carboxamide;
(S)-2-Amino-N-{[1-(8-trifluoromethanesulphonyloxy-1,4-benzodioxan-2-ylmethyl)-4-piperidyl]methyl}pyridine-3-carboxamide;
(S)-N-{[1-(7-Methyl-1,4-benzodioxan-2-ylmethyl)-4-piperidyl]methyl}pyridine-3-carboxamide;
(S)-2-Methyl- N-{[1-(7-methyl-1,4-benzodioxan-2-ylmethyl)-4-piperidyl]methyl}pyridine-3-carboxamide;
(S)-N-{[1-(7-Methyl-1,4-benzodioxan-2-ylmethyl)-4-piperidyl]methyl}-6-(1-pyrrolyl)pyridine-3-carboxamide;
(S)-N-{[1-(7-Methyl-1,4-benzodioxan-2-ylmethyl)-4-piperidyl]methyl}-2-(methylthio)pyridine-3-carboxamide;
(S)-5-Bromo-N-{[1-(7-methyl-1,4-benzodioxan-2-ylmethyl)-4-piperidyl]methyl}pyridine-3-carboxamide;
(S)-N-{[1-(7-Bromo-1,4-benzodioxan-2-ylmethyl)-4-piperidyl]methyl}pyridine-3-carboxamide;
(S)-N-{[1-(7-Bromo-1,4-benzodioxan-2-ylmethyl)-4-piperidyl]methyl}-2-methylpyridine-3-carboxamide;

(S)-N-{[1-(7-Bromo-1,4-benzodioxan-2-ylmethyl)-4-piperidyl]methyl}-6-(1-pyrrolyl)pyridine-3-carboxamide;

(S)-N-{[1-(7-Bromo-1,4-benzodioxan-2-ylmethyl)-4-piperidyl]methyl}-2-(methylthio)pyridine-3-carboxamide;

(S)-5-Bromo-N-{[1-(7-bromo-1,4-benzodioxan-2-ylmethyl)-4-piperidyl]methyl}pyridine-3-carboxamide;

(S)-N-{[1-(7-Chloro-1,4-benzodioxan-2-ylmethyl)-4-piperidyl]methyl}-6-(1-pyrrolyl)pyridine-3-carboxamide;

(S)-N-{[1-(7-Chloro-1,4-benzodioxan-2-ylmethyl)-4-piperidyl]methyl}-2-(methylthio)pyridine-3-carboxamide;

(S)-5-Bromo-N-{[1-(7-chloro-1,4-benzodioxan-2-ylmethyl)-4-piperidyl]methyl}pyridine-3-carboxamide;

(S)-N-{[1-(7-Fluoro-1,4-benzodioxan-2-ylmethyl)-4-piperidyl]methyl}pyridine-3-carboxamide;

(S)-N-{[1-(7-Fluoro-1,4-benzodioxan-2-ylmethyl)-4-piperidyl]methyl}-2-(methylthio)pyridine-3-carboxamide;

(S)-N-{[1-(8-Trifluoromethyl-1,4-benzodioxan-2-ylmethyl)-4-piperidyl]methyl}pyridine-3-carboxamide;

(S)-2-Methyl-N-{[1-(8-trifluoromethyl-1,4-benzodioxan-2-ylmethyl)-4-piperidyl]methyl}pyridine-3-carboxamide;

(S)-6-(1-Pyrrolyl)-N-{[1-(8-trifluoromethyl-1,4-benzodioxan-2-ylmethyl)-4-piperidyl]methyl}pyridine-3-carboxamide;

(S)-2-(Methylthio)-N-{[1-(8-trifluoromethyl-1,4-benzodioxan-2-ylmethyl)-4-piperidyl]methyl}pyridine-3-carboxamide;

(S)-5-Bromo-N-{[1-(8-trifluoromethyl-1,4-benzodioxan-2-ylmethyl)-4-piperidyl]methyl}pyridine-3-carboxamide;

(S)-N-{[1-(8-Chloro-1,4-benzodioxan-2-ylmethyl)-4-piperidyl]methyl}-6-(1-pyrrolyl)pyridine-3-carboxamide;

(S)-N-{[1-(8-Chloro-1,4-benzodioxan-2-ylmethyl)-4-piperidyl]methyl}-2-(methylthio)pyridine-3-carboxamide;

(S)-5-Bromo-N-{[1-(8-chloro-1,4-benzodioxan-2-ylmethyl)-4-piperidyl]methyl}pyridine-3-carboxamide;

and pharmaceutically acceptable salts thereof.

The present invention also includes pharmaceutical compositions containing a therapeutically effective amount of a compound of formula I or a salt thereof together with a pharmaceutically acceptable diluent or carrier.

As used hereinafter, the term "active compound" denotes a compound of formula I or a salt thereof. In therapeutic use, the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention may contain 0.1–99% by weight of active compound. The compositions of the invention are generally prepared in unit dosage form. Preferably the unit dosage of active ingredient is 1–500 mg. The excipients used in the preparation of these compositions are the excipients known in the pharmacist's art.

Compositions for oral administration are the preferred compositions of the invention and these are the known pharmaceutical forms for such administration, for example tablets, capsules, syrups and aqueous or oil suspensions. The excipients used in the preparation of these compositions are the excipients known in the pharmacist's art. Tablets may be prepared by mixing the active compound with an inert diluent such as calcium phosphate in the presence of disintegrating agents, for example maize starch, and lubricating agents, for example magnesium stearate, and tableting the mixture by known methods. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by conventional means and, if desired, provided with enteric coatings in a known manner. The tablets and capsules may conveniently each contain 1 to 500 mg of the active compound. Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil.

The active compound may be formulated into granules with or without additional excipients. The granules may be ingested directly by the patient or they may be added to a suitable liquid carrier (for example water) before ingestion. The granules may contain disintegrants (for example a pharmaceutically acceptable effervescent couple formed from an acid and a carbonate or bicarbonate salt) to facilitate dispersion in the liquid medium.

Compositions of the invention suitable for rectal administration are the known pharmaceutical forms for such administration, for example, suppositories with cocoa butter or polyethylene glycol bases.

Compositions of the invention suitable for parenteral administration are the known pharmaceutical forms for such administration, for example sterile suspensions or sterile solutions in a suitable solvent.

Compositions for topical administration may comprise a matrix in which the pharmacologically active compounds of the present invention are dispersed so that the compounds are held in contact with the skin in order to administer the compounds transdermally. A suitable transdermal composition may be prepared by mixing the pharmaceutically active compound with a topical vehicle, such as a mineral oil, petrolatum and/or a wax, for example paraffin wax or beeswax, together with a potential transdermal accelerant such as dimethyl sulphoxide or propylene glycol. Alternatively the active compounds may be dispersed in a pharmaceutically acceptable cream or ointment base. The amount of active compound contained in a topical formulation should be such that a therapeutically effective amount of the compound is delivered during the period of time for which the topical formulation is intended to be on the skin.

The compounds of the present invention may also be administered by continuous infusion either from an external source, for example by intravenous infusion or from a source of the compound placed within the body. Internal sources include implanted reservoirs containing the compound to be infused which is continuously released for example by osmosis and implants which may be (a) liquid such as a suspension or solution in a pharmaceutically acceptable oil of the compound to be infused for example in the form of a very sparingly water-soluble derivative such as a dodecanoate salt or ester or (b) solid in the form of an implanted support, for example of a synthetic resin or waxy material, for the compound to be infused. The support may be a single body containing all the compound or a series of several bodies each containing part of the compound to be delivered. The amount of active compound present in an internal source should be such that a therapeutically effective amount of the compound is delivered over a long period of time.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The present invention also comprises the use of a compound of formula I as a medicament.

The compounds of formula I or a salt thereof or pharmaceutical compositions containing a therapeutically effective amount thereof may be used in the treatment of depression, anxiety, psychoses (for example schizophrenia), tardive dyskinesia, Parkinson's disease, obesity, hypertension, Tourette's syndrome, sexual dysfunction, drug addiction, drug abuse, cognitive disorders, Alzheimers disease, senile dementia, obsessive-compulsive behaviour, panic attacks, social phobias, eating disorders, anorexia, cardiovascular and cerebrovascular disorders, non-insulin dependent diabetes mellitus, hyperglycaemia, constipation, arrhythmia, disorders of the neuroendocrine system, stress, prostatic hypertrophy, and spasticity in human beings. Whilst the precise amount of active compound administered in such treatment will depend on a number of factors, for example the age of the patient, the severity of the condition and the past medical history and always lies within the sound discretion of the administering physician, the amount of active compound administered per day is in the range 1 to 1000 mg preferably 5 to 500 mg given in single or divided doses at one or more times during the day.

Preferably, the compounds of formula I or a salt thereof or pharmaceutical compositions containing a therapeutically effective amount thereof are used in the treatment of depression, anxiety, psychoses (for example schizophrenia), tardive dyskinesia, Parkinson's disease, hypertension, Tourette's syndrome, obsessive-compulsive behaviour, panic attacks, social phobias, cardiovascular and cerebrovasular disorders, stress and prostatic hypertrophy in mammals particularly human beings.

A further aspect of the present invention provides the use of a compound of formula I or a salt thereof in the manufacture of a medicament for treating depression, anxiety, psychoses (for example schizophrenia), tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behaviour, panic attacks, social phobias, eating disorders and anorexia, cardiovascular and cerebrovascular disorders, non-insulin dependent diabetes mellitus, hyperglycaemia, constipation, arrhythmia, disorders of the neuroendocrine system, stress, prostatic hypertrophy, or spasticity in mammals, particularly human beings.

Preferably, the compound of formula I or a salt thereof is used in the manufacture of a medicament for the treatment of depression, anxiety, psychoses (for example schizophrenia), tardive dyskinesia, Parkinson's disease, hypertension, Tourette's syndrome, obsessive-compulsive behaviour, panic attacks, social phobias, cardiovascular and cerebrovasular disorders, stress and prostatic hypertrophy.

The present invention also provides a method of treating depression, anxiety, psychoses (for example schizophrenia), tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behaviour, panic attacks, social phobias, eating disorders and anorexia, cardiovascular and cerebrovascular disorders, non-insulin dependent diabetes mellitus, hyperglycaemia, constipation, arrhythmia, disorders of the neuroendocrine system, stress, prostatic hypertrophy, or spasticity which comprises the administration of a therapeutically effective amount of a compound of formula I to a mammal particularly a human being, in need thereof.

Preferably, the method is a method of treating depression, anxiety, psychoses (for example schizophrenia), tardive dyskinesia, Parkinson's disease, hypertension, Tourette's syndrome, obsessive-compulsive behaviour, panic attacks, social phobias, cardiovascular and cerebrovasular disorders, stress and prostatic hypertrophy.

Processes for the preparation of compounds of formula I will now be described. These processes form a further aspect of the present invention. The processes are preferrably carried out at atmospheric pressure.

Compounds of formula I in which Q is a group of formula IIa in which $R_5$ is H, and V is $(CH_2)_{n+1}$, wherein n is 0,1 or 2 may be prepared by the reaction of a compound of formula III

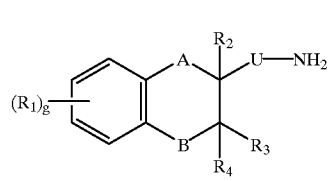

III with a compound of formula IV

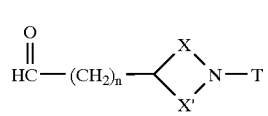

IV followed by reaction of the intermediate imine with a reducing agent, for example sodium borohydride.

Compounds of formula I in which Q is a group of formula IIa in which $R_5$ is H, and V is $(CH_2)_{n+1}$ wherein n is 0,1 or 2 may be prepared by the reaction of a compound of formula III with a compound of formula V

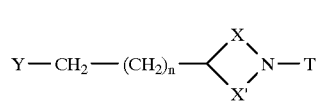

V in which Y is a leaving group, for example toluene-4-sulphonyloxy, optionally in the presence of a suitable solvent, optionally in the presence of a base, for example potassium carbonate.

Compounds of formula I in which Q is a group of formula IIa in which $R_5$ is H, and V is $(CH_2)_{n+1}$ wherein n is 0,1 or 2 may be prepared by reaction of a compound of formula VI

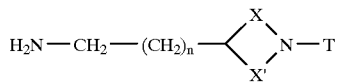

VI with a compound of formula VII

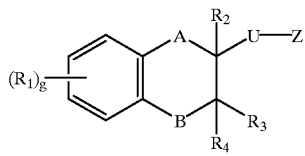

VII in which Z is a leaving group, for example toluene-4-sulphonyloxy, optionally in the presence of a suitable solvent, optionally in the presence of a base, for example potassium carbonate.

Compounds of formula I in which U is methylene and Q is a group of formula IIa in which $R_5$ is H, and V is $(CH_2)_{n+1}$ wherein n is 0, 1 or 2 may be prepared by reaction of a compound of formula VIII

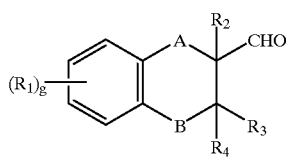

VIII with a compound of formula VI, followed by reduction of the intermediate imine with a suitable reducing agent, for example sodium borohydride.

Compounds of formula I in which $R_5$ is an alkyl group may be prepared by alkylation of a compound of formula I in which $R_5$ is H with for example formaldehyde and formic acid, or an aldehyde and a reducing agent such as sodium cyanoborohydride.

Compounds of formula III, in which U is $(CH_2)_{m+1}$ wherein m is 0, 1 or 2 may be prepared by reduction of a compound of formula IX

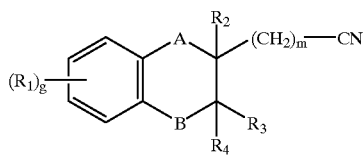

IX with a reducing agent, for example lithium aluminium hydride.

Compounds of formula IX in which A and B are both O may be prepared by reaction of a compound of formula X

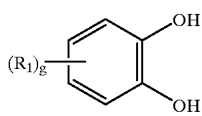

X with a vicinally disubstituted nitrile compound of formula XI

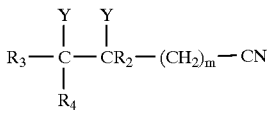

XI in which Y is a leaving group such as halo, for example bromo, in the presence of a base, for example potassium carbonate.

Compounds of formula III may be prepared from compounds of formula XII

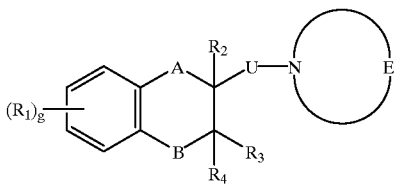

XII in which E together with the nitrogen atom to which it is attached is a cyclic imide, for example a phthalimide, by acid or base catalysed hydrolysis or by cleavage with a reagent, for example hydrazine hydrate.

Compounds of formula XII in which E together with the nitrogen atom to which it is attached is a phthalimide may be prepared by reaction of a compound of formula VII in which Z is a leaving group, for example toluene-4-sulphonyloxy, with potassium phthalimide.

Compounds of formula III in which U is methylene may be prepared by reduction of a compound of formula XIII

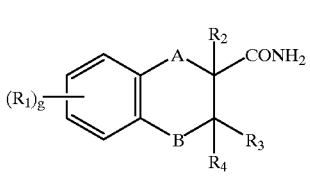

XIII with a suitable reducing agent, for example lithium aluminium hydride.

Compounds of formula XIII may be prepared by reaction of a compound of formula XIV

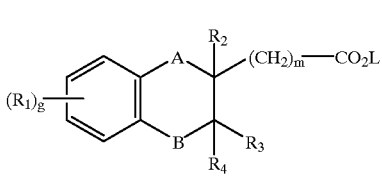

XIV in which m is 0 and L is an alkyl group containing 1 to 6 carbon atoms with ammonia.

Compounds of formula IV may be prepared by reaction of a compound of formula XV

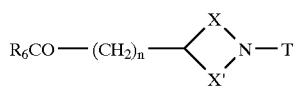

XV in which $R_6$ is an alkoxy group containing 1 to 4 carbon atoms, with a reducing agent, for example sodium bis (2-methoxyethoxy)aluminium hydride in a solvent, for example toluene.

Compounds of formula XV may be prepared by reaction of a compound of formula XVI

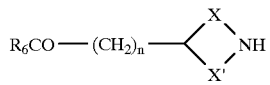

XVI with an acylating agent of formula X"-CO.HET in which X" is a leaving group, for example halo, alkoxy, hydroxy or alkoxycarbonyloxy, in the presence of a base, for example triethylamine, or an amide bond forming agent, for example carbonyl diimidazole, in a suitable solvent such as dichloromethane.

Compounds of formula IV may also be prepared by oxidation of a compound of formula XVII

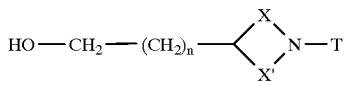

XVII with a suitable oxidising agent, for example oxalyl chloride/dimethyl sulphoxide.

Compounds of formula V in which Y is toluene-4-sulphonyloxy may be prepared by reaction of a compound of formula XVII with a tosylating agent, for example toluene-4-sulphonyl chloride.

Compounds of formula XVII may be prepared by reaction of a compound of formula XVIII

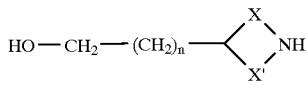

XVIII with an acylating agent of formula X"-CO.HET in which X" is a leaving group, for example halo, alkoxy, hydroxy or alkoxycarbonyloxy, in the presence of a base, for example triethylamine, or an amide bond forming agent, for example carbonyl diimidazole, in a suitable solvent such as dichloromethane.

Compounds of formula XVIII may be prepared by reduction of a compound of formula XVI, in which $R_6$ is an alkoxy group containing 1 to 4 carbon atoms, with a reducing agent, for example lithium aluminium hydride.

Compounds of formula VI may be prepared by reaction of a compound of formula XIX

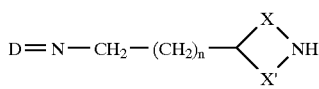

XIX in which D is a protecting group, for example 5-bromo-2-hydroxybenzylidene, with an acylating agent of formula X"-CO.HET in which X" is a leaving group, for example halo, alkoxy, hydroxy or alkoxycarbonyloxy, in the presence of a base, for example triethylamine, or an amide bond forming agent, for example carbonyl diimidazole, in a suitable solvent such as dichloromethane, followed by removal of the protecting group, for example by acid-catalysed hydrolysis.

Compounds of formula XIX may be prepared by reaction of a compound of formula XX

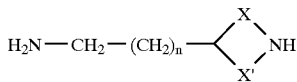

XX with a protecting reagent, for example 5-bromo-2-hydroxybenzaldehyde.

Compounds of formula XX may be prepared by reduction of a compound of formula XVI in which $R_6$ is $NH_2$ with a reducing agent, for example lithium aluminium hydride.

Compounds of formula VII in which Z is toluene-4-sulphonyloxy may be prepared by reaction of a compound of formula XXI

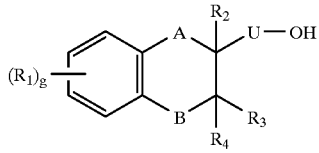

XXI with toluene-4-sulphonyl chloride, optionally in the presence of a base, for example pyridine.

Compounds of formula XXI in which U is $(CH_2)_{m+1}$ may be prepared by reduction of a compound of formula XIV in which L is an alkyl group containing 1 to 4 carbon atoms and m is 0, 1 or 2, with a reducing agent, for example lithium aluminium hydride.

Compounds of formula XXI in which A and B are both —O—, $R_2$, $R_3$ and $R_4$ are all H, and U is methylene may be prepared by reaction of a compound of formula XXII

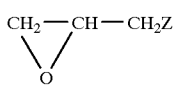

XXII in which Z is a leaving group, for example chloro or toluene-4-sulphonyloxy, with a compound of formula X in a suitable solvent, for example water or dimethylformamide in the presence of a base, for example sodium hydroxide. When an enantiomerically pure form of a compound of formula XXII, for example (R)-glycidyl-4-toluenesulphonate, is used, the single (S)-enantiomer of a compound of formula XXI can be prepared.

Compounds of formula XXI in which A and B are both —O—, U is methylene, $R_2$, $R_3$ and $R_4$ are all H, and $R_1$ is an alkoxy group containing 1 to 3 carbon atoms may be prepared by alkylation of the corresponding compound of formula XXI in which $R_1$ is hydroxy by reaction with an alkylating agent, for example methyl iodide, in the presence of a base, for example sodium hydroxide.

Compounds of formula XXI in which A and B are both —O—, U is methylene, and $R_2$, $R_3$ and $R_4$ are all H, may also be prepared by cyclisation of a compound of formula XXIII

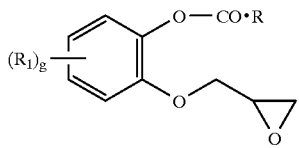

XXIII in which R is H or an alkyl group containing 1 to 4 carbon atoms, using a base for example sodium methoxide.

Compounds of formula XXIII may be prepared by oxidation of compounds of formula XXIV

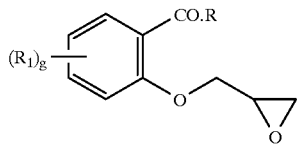

XXIV with a peroxyacid, for example 3-chloroperoxybenzoic acid.

Compounds of formula XXIV may be prepared by alkylating compounds of formula XXV

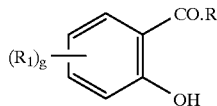

XXV with compounds of formula XXII, in which Z is a leaving group, for example chloro or toluene-4-sulphonyloxy, in a suitable solvent, for example dimethylformamide, in the presence of a base, for example potassium carbonate.

Compounds of formula XXI in which A and B are both —O—, U is methylene, $R_2$ is alkyl and $R_3$ and $R_4$ are H may be prepared by reaction of a compound of formula XXVI

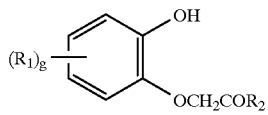

XXVI with a reagent suitable for the conversion of carbonyl compounds into epoxides, for example dimethylsulphoxonium methylide.

Compounds of formula XXVI may be prepared by reaction of a compound of formula X with a halomethyl ketone, for example $ClCH_2COR_2$, in the presence of a base, for example potassium carbonate.

Compounds of formula XXI in which A and U are methylene, B is —O— and $R_2$ is H, may be prepared by reduction of a compound of formula XXVII

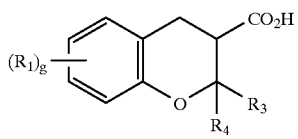

XXVII with a reducing agent, for example borane-dimethyl sulphide complex.

Compounds of formula XXVII may be prepared by reduction of a compound of formula XXVIII

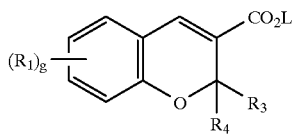

XXVIII in which L is H with a reducing agent, for example hydrogen in the presence of a palladium-on-carbon catalyst.

Compounds of formula XXVIII in which L is H may be prepared by acid or base-catalysed hydrolysis of a compound of formula XXVIII in which L is an alkyl group containing 1 to 6 carbon atoms.

Compounds of formula XXVIII in which L is an alkyl group may be prepared by reaction of a compound of formula XXIX

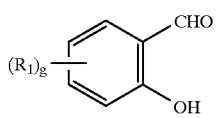

XXIX with a compound of formula XXX

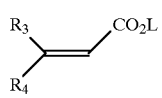

XXX in which L is an alkyl group containing 1 to 6 carbon atoms, in the presence of a base, for example 1,4-diazabicyclo [2.2.2]octane (DABCO).

Compounds of formula XXIX may be prepared by reaction of a compound of formula XXXI

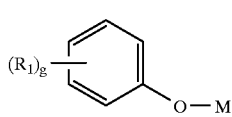

XXXI in which M is an O-protecting group, for example a 1-ethoxyethyl group, with a metallating agent, for example n-butyllithium, followed by a formylating agent, for example dimethylformamide.

Compounds of formula XXI in which A, B and U are methylene and $R_2$, $R_3$, and $R_4$ are H may be prepared by reduction of a compound of formula XXXII

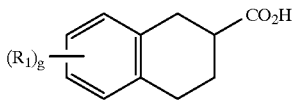

XXXII with a reducing agent, for example borane-dimethyl sulphide complex.

Compounds of formula XXXII may be prepared by Birch reduction of a compound of formula XXXIII

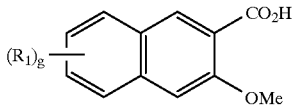

XXXIII with, for example, lithium in liquid ammonia.

Compounds of formula XXXIII may be prepared by reaction of a compound of formula XXXIV

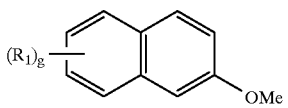

XXXIV with a metallating agent, for example n-butyllithium, followed by carbon dioxide, followed by acidification of the intermediate carboxylic acid salt.

Compounds of formula VIII may be prepared by oxidation of a compound of formula XXI in which U is methylene with a suitable oxidising agent, for example pyridinium chlorochromate or by reduction of a compound of formula XIV wherein m is 0 with a suitable reducing agent, for example sodium bis(2-methoxyethoxy)aluminium hydride in a solvent, for example toluene.

Compounds of formula XIV in which A and B are both —O— may be prepared by reaction of a compound of formula XXXV

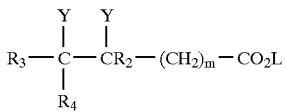

XXXV in which Y is a leaving group, for example bromo, and L is an alkyl group containing 1 to 6 carbon atoms with a compound of formula X, in the presence of a base, for example potassium carbonate.

Compounds of formula XIV in which A is methylene, B is —O—, m is 0, $R_2$ is H and L is an alkyl group containing 1 to 6 carbon atoms may be prepared by reduction of a compound of formula XXVIII in which L is an alkyl group containing 1 to 6 carbon atoms, with a suitable reducing agent, for example hydrogen in the presence of a palladium-on-carbon catalyst.

Compounds of formula XIV is which A and B are both methylene, m is 0, $R_2$ is H and L is an alkyl group containing 1 to 6 carbon atoms may be prepared by esterfication of a compound of formula XXXII with an alcohol of formula LOH, optionally in the presence of an acid or base catalyst.

Compounds of formula I in which Q is a group of formula IIa may be prepared by reaction of compound of formula XXXVI

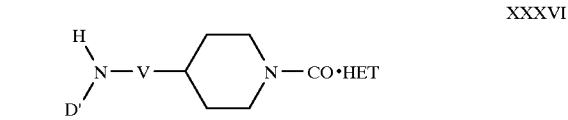

XXXVI in which D' is H, with a compound of formula VII in which Z is a leaving group, for example toluene-4-sulphonyloxy, optionally in the presence of a base, for example potassium carbonate, and optionally in a solvent, for example acetonitrile.

Compounds of formula XXXVI in which D' is H may be prepared by deprotection of a compound of formula XXXVI in which D' is a protecting group, for example tert-butoxycarbonyl, for example by acid hydrolysis in the presence of an acid, for example trifluoroacetic acid.

Compounds of formula XXXVI in which D' is a protecting group may be prepared by reaction of a compound of formula XXXVII

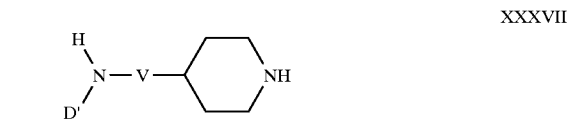

XXXVII in which D' is a protecting group, for example tert-butoxycarbonyl, with a compound of formula X".CO.HET in which X" is a leaving group, for example halo, alkoxy, hydroxy or alkoxycarbonyloxy, in the presence of a base, for example triethylamine, or an amide bond forming agent, for example carbonyl diimidazole, in a suitable solvent such as dichloromethane.

Compounds of formula XXXVI in which D' is a protecting group and HET is of the formula XXXVIII

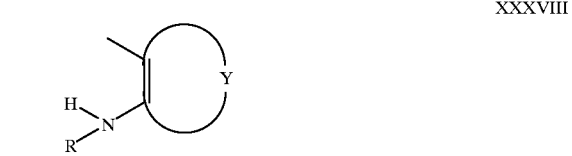

XXXVIII in which Y completes a heteroaromatic ring and R is H or alkyl, may be prepared by reaction of a compound of formula XXXVII with a compound of formula XXXIX

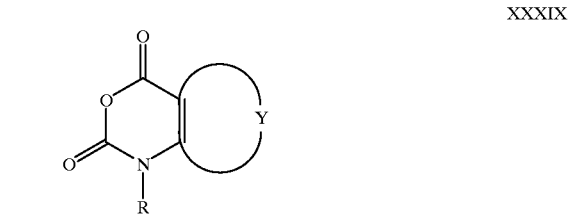

XXXIX in which Y completes a heteroaromatic ring and R is H or an alkyl group, in a solvent, for example 1,2-dimethoxyethane.

Compounds of formula I in which Q is a group of formula IIb may be prepared by reaction of a compound of formula XL

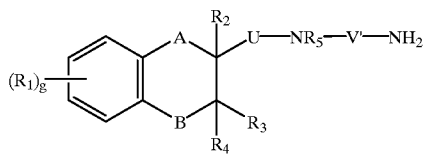

XL with an acylating agent of formula X"-CO.HET in which X" is a leaving group, for example halo, alkoxy, hydroxy or alkoxycarbonyloxy, in the presence of a base, for example triethylamine, or an amide bond forming agent, for example carbonyl diimidazole, in a suitable solvent such as dichloromethane.

Compounds of formula I in which Q is a group of formula IIb may be prepared by reaction of a compound of formula VII in which Z is a leaving group, for example toluene-4-sulphonyloxy with a compound of formula XLI

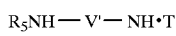

XLI optionally in the presence of a base, for example potassium carbonate.

Compounds of formula XL may be prepared from a compound of formula XLII

XLII

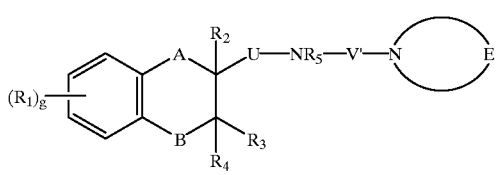

in which E together with the nitrogen atom to which it is attached is a cyclic imide, for example a phthalimide, by acid or base catalysed hydrolysis or by cleavage with a reagent, for example hydrazine hydrate.

Compounds of formula XLII in which E together with the nitrogen atom to which it is attached is a phthalimide and $R_5$ is H may be prepared by reaction of a compound of formula III with a haloalkyl phthalimide, for example N-(3-bromopropyl)phthalimide, optionally in the presence of a base, for example potassium carbonate.

Compounds of formula I in which Q is a group of formula IIb may be prepared by reaction of a compound of formula XLIII

XLIII

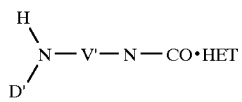

In which D' is H, with a compound of formula VII in which Z is a leaving group, for example toluene-4-sulphonyloxy, optionally in the presence of a base, for example potassium carbonate, and optionally in a solvent, for example acetonitrile.

Compounds of formula XLIII in which D' is H may be prepared by deprotection of a compound of formula XLIII in which D' is a protecting group, for example tert-butoxycarbonyl, for example by acid hydrolysis in the presence of an acid, for example trifluoroacetic acid.

Compounds of formula XLIII in which D' is a protecting group may be prepared by reaction of a compound of formula XLIV

XLIV

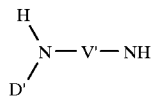

in which D' is a protecting group, for example tert-butoxycarbonyl, with a compound of formula X".CO.HET in which X" is a leaving group, for example halo, alkoxy, hydroxy or alkoxycarbonyloxy, in the presence of a base, for example triethylamine, or an amide bond forming agent, for example carbonyl diimidazole, in a suitable solvent such as dichloromethane.

Compounds of formula XLIII in which D' is a protecting group and HET is of the formula XXXVIII in which Y completes a heteroaromatic ring and R is H or alkyl, may be prepared by reaction of a compound of formula XLIV with a compound of formula XXXIX in which Y completes a heteroaromatic ring and R is H or an alkyl group, in a solvent, for example 1,2-dimethoxyethane.

Compounds of formula I in which Q is a group of formula IIc may be prepared by reaction of a compound of formula XLV

XLV

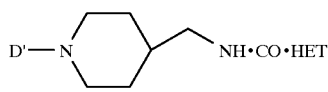

in which D' is H, with a compound of formula VII in which Z is a leaving group, for example toluene-4-sulphonyloxy, optionally in the presence of a base, for example potassium carbonate, and optionally in a solvent, for example acetonitrile.

Compounds of formula XLV in which D' is H may be prepared by deprotection of a compound of formula XLV in which D' is a protecting group, for example tert-butoxycarbonyl, for example by acid hydrolysis in the presence of an acid, for example trifluoroacetic acid.

Compounds of formula XLV in which D' is a protecting group may be prepared by reaction of a compound of formula XLVI

XLVI

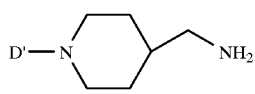

in which D' is a protecting group, for example tert-butoxycarbonyl, with a compound of formula X".CO.HET in which X" is a leaving group, for example halo, alkoxy, hydroxy or alkoxycarbonyloxy, in the presence of a base, for example triethylamine, or an amide bond forming agent, for example carbonyl diimidazole, in a suitable solvent such as dichloromethane.

Compounds of formula XLV in which D' is a protecting group and Het is of the formula XXXVIII in which Y completes a heteroaromatic ring and R is H or alkyl, may be prepared by reaction of a compound of formula XLVI with a compound of formula XXXIX in which Y completes a heteroaromatic ring and R is H or alkyl, in a solvent for example 1,2-dimethoxyethane.

Compounds of formula I in which Q is a group of formula IIc may be prepared by reaction of a compound of formula XLVII

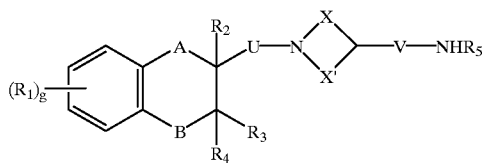

XLVII with a compound of formula XXXIX, for example pyrido [2,3-d][1,3]oxazine-2,4(1H)-dione optionally in the presence of a solvent, for example 1,2-dimethoxyethane.

Compounds of formula XLVII in which $R_5$ is H may be prepared from compounds of formula XLVIII

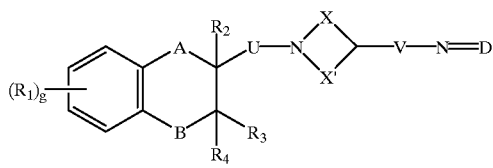

XLVIII in which D is a protecting group, for example 5-bromo-2-hydroxybenzylidene, by acid or base catalysed hydrolysis.

Compounds of formula XLVIII may be prepared by reaction of a compound of formula XLIX

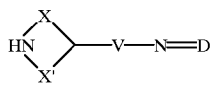

XLIX in which D is a protecting group, for example 5-bromo-2-hydroxybenzylidene, with a compound of formula VII, optionally in the presence of a base, for example triethylamine.

Compounds of formula XLIX may be prepared by reaction of a compound of formula L

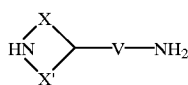

L with a protecting reagent, for example 5-bromo-2-hydroxybenzaldehyde.

Compounds of formula I in which Q is a group of formula IIc may also be prepared by reaction of a compound of formula XLVII with an acylating agent of formula X"-CO.HET in which X" is a leaving group, for example halo, alkoxy, hydroxy or alkoxycarbonyloxy, in the presence of a base, for example triethylamine, or an amide bond forming agent, for example carbonyl diimidazole or N,N'-diisopropylcarbodiimide, in a suitable solvent such as dichloromethane.

The ability of compounds of formula I to interact with 5-hydroxytryptamine (5-HT) receptors has been demonstrated by the following test which determines the ability of the compounds to inhibit tritiated ligand binding to 5-HT receptors in vitro and in particular to $5-HT_{1A}$ receptors.

Hippocampal tissue from the brains of male Sprague-Dawley rats (Charles River; weight range 150–250 g) was homogenised in ice-cold 50 mM Tris-HCl buffer (pH 7.7 when measured at 25° C., 1:40 w/v) and centrifuged at 30,000 g at 4° C. for 10 minutes. The pellet was rehomogenised in the same buffer, incubated at 37° C. for 10 minutes and centrifuged at 30,000 g at 4° C. for 10 minutes. The final pellet was resuspended in 50 mM Tris-HCl buffer (pH 7.7) containing 4 mM $CaCl_2$, 0.1% L-ascorbic acid and 10 μM pargyline hydrochloride (equivalent to 6.25 mg wet weight of tissue/ml) and used immediately in the binding assay. Aliquots (400 μl; equivalent to 2.5 mg wet weight of tissue/tube) of this suspension were added to tubes containing the ligand (50 μl; 2 nM) and distilled water (50 μl total binding) or 5-HT (50 μl; 10 μM; non-specific binding) or test compound (50 μl; at a single concentration of $10^{-6}$ M or at 10 concentrations ranging from $10^{-11}$–$10^{-3}$ M). The ligand was [$^3$H]8-hydroxy-2-(dipropylamino)tetralin ([$^3$H]8-OH-DPAT) and the mixture was incubated at 25° C. for 30 minutes before the incubation was terminated by rapid filtration.

The filters were washed with ice-cold Tris-HCl buffer and dried. The filters were punched out into vials, scintillation fluid added and radioactivity determined by liquid scintillation counting. The percentage displacement of specific binding of the tritiated ligand was calculated for the single concentration ($10^{-6}$ M) of test compound. Displacement curves were then produced for those compounds which displaced ≧50% of specific binding of the tritiated ligand at $10^{-6}$ M using a range of concentrations of the compound. The concentration which gave 50% inhibition of specific binding ($IC_{50}$) was obtained from the curve. The inhibition coefficient $K_i$ was then calculated using the formula $$K_i = \frac{IC_{50}}{1 + ([\text{ligand}]/K_D)}$$

in which [ligand] is the concentration of the tritiated ligand used and $K_D$ is the equilibrium dissociation constant for the ligand.

The ability of compounds of formula I to interact with adrenoceptor binding sites has been demonstrated by the following test which determines the ability of the compounds to inhibit tritiated ligand binding to adrenoceptors in vitro and in particular $\alpha_1$-adrenoceptors.

Whole cortical tissue from the brains of male Charles River CD rats weighing between 150–250 g were homogenised in ice-cold 50 mM Tris-HCl, pH 7.6 (at 25° C.; 1:40 w/v) and centrifuged at 1000 g at 4° C. for 10 minutes. The supernatant was centrifuged at 30,000 g at 4° C. for 10 minutes. The pellet was rehomogenised in 50 mM Tris-HCl, pH 7.6 (1:40 w/v) and centrifuged at 30,000 g at 4° C. for 10 minutes. The final pellet was resuspended in 50 mM Tris-HCl, pH 7.6 (equivalent to 12.5 mg wet weight of tissue/ml) and used immediately in the binding assay. Aliquots (400 μl; equivalent to 5 mg wet weight of tissue/tube) of this suspension were added to tubes containing the ligand (50 μl; 0.1 nM) and distilled water (50 μl; total binding) or phentolamine (50 μl; 5 μM; non-specific binding) or test compound (50 μl; at a single concentration of $10^{-6}$M or at 10 concentrations ranging from $10^{-11}$–$10^{-3}$M). The ligand was [7-methoxy-$^3$H]prazosin and the mixture was incubated at 30° C. for 30 minutes before the incubation was terminated by rapid filtration.

The filters were washed with ice-cold Tris-HCl buffer and dried. The filters were punched out into vials, scintillation fluid added and radioactivity determined by liquid scintillation counting. The percentage displacement of specific binding of the tritiated ligand was calculated for the single concentration ($10^{-6}$ M) of test compound. Displacement curves were then produced for those compounds which displaced $\geq 50\%$ of specific binding of the tritiated ligand at $10^{-6}$ M using a range of concentrations of the compound. The concentration which gave 50% inhibition of specific binding ($IC_{50}$) was obtained from the curve. The inhibition coefficient $K_i$ was then calculated using the formula $$K_i = \frac{IC_{50}}{1 + ([\text{ligand}]/K_D)}$$

in which [ligand] is the concentration of the tritiated ligand used and $K_D$ is the equilibrium dissociation constant for the ligand.

The ability of compounds of formula I to interact with $\alpha_2$-adrenoceptor binding sites has been demonstrated by the following test which determines the ability of the compounds to inhibit tritiated ligand binding to $\alpha_2$-adrenoceptors in vitro and in particular to $\alpha_{2A}$-adrenoceptors.

Human cerebral cortex obtained at post-mortem was homogenised in ice-cold 0.25M sucrose (1:30 w/v) and centrifuged at 1,000 g at 4° C. for 12 minutes. The supernatant was stored on ice and the pellet was rehomogenised in 0.25M sucrose (1:15 w/v) and centrifuged at 850 g at 4° C. for 12 minutes. Combined supernatants were diluted with 5mM Tris-HCl (pH 7.5) containing 5 mM ethylenediamine tetraacetic acid (EDTA), readjusted to pH 7.5 (at 25° C.) with 1M sodium hydroxide to 1:80 w/v, and centrifuged at 11,000 g at 4° C. for 10 minutes. The resulting pellet was resuspended in 50 mM Tris-HCl (pH 7.5) containing 5.68 mM L-ascorbic acid and 0.5 mM EDTA, readjusted to pH 7.5 (at 25° C.) with 1 M sodium hydroxide to 1:80 w/v, and centrifuged at 11,000 g for 10 minutes. The pellet was stored at $-80°$ C. On the day of the assay the pellet was thawed, resuspended in 50 mM Tris-HCl (pH 7.5) containing 5.68 mM L-ascorbic acid and 5 mM EDTA to 1:80 w/v and centrifuged at 11,000 g for 10 minutes. The final pellet was resuspended in 50 mM Tris-HCl (pH 7.5) containing 5.68 mM L-ascorbic acid and 5 mM EDTA (equivalent to 25 mg wet weight of tissue/ml).

Aliquots (400 µl; equivalent to 10 mg wet weight of tissue/tube) of this suspension were added to tubes containing the ligand (50 µl; 0.2 nM) and distilled water (50 µl; total binding) or phentolamine (50 µl; 50 µM; non-specific binding) or test compound (50 µl; at a single concentration of $10^{-6}$M or at 10 concentrations ranging from $10^{-11}$–$10^{-3}$M). The ligand was tritiated RX 821002 (2-(2-methoxy-1,4-[6,7(n)-$^3$H]benzodioxan-2-yl)-2-imidazoline) and the mixture was incubated at 0° C. for 75 minutes before the incubation was terminated by rapid filtration.

The filters were washed with ice-cold Tris-HCl buffer and dried. The filters were punched out into vials, scintillation fluid added and radioactivity determined by liquid scintillation counting. The percentage displacement of specific binding of the tritiated ligand was calculated for the single concentration ($10^{-6}$M) of test compound. Displacement curves were then produced for those compounds which displaced $\geq 50\%$ of specific binding of the tritiated ligand at $10^{-6}$ M using a range of concentrations of the compound. The concentration which gave 50% inhibition of specific binding ($IC_{50}$) was obtained from the curve. The inhibition coefficient $K_i$ was then calculated using the formula $$K_i = \frac{IC_{50}}{1 + ([\text{ligand}]/K_D)}$$

in which [ligand] is the concentration of the tritiated ligand used and $K_D$ is the equilibrium dissociation constant for the ligand.

The ability of compounds of formula I to interact with adrenoceptor binding sites has been demonstrated by the following test which determines the ability of the compounds to inhibit tritiated ligand binding to adrenoceptors in vitro and in particular to $\alpha_{2D}$-adrenoceptors.

Frontal cortical tissue from the brains of male Charles River CD rats weighing between 150–250 g were homogenised in ice-cold 0.25 M sucrose (1:30 w/v) and centrifuged at 1,000 g at 4° C. for 12 minutes. The supernatant was stored on ice and the pellet was rehomogenised in 0.25 M sucrose (1:15 w/v) and centrifuged at 850 g at 4° C. for 12 minutes. Combined supernatants were diluted with 5 mM Tris-HCl (pH 7.5) containing 5 mM ethylenediamine tetraacetic acid (EDTA) readjusted to pH 7.5 (at 25° C.) with 1 M sodium hydroxide to 1:80 w/v, and centrifuged at 30,000 g at 4° C. for 10 minutes. The resulting pellet was resuspended in 50 mM Tris-HCl (pH 7.5) containing 5.68 mM L-ascorbic acid and 0.5 mM EDTA readjusted to pH 7.5 (at 25° C.) with 1 M sodium hydroxide, and centrifuged at 30,000 g for 10 minutes. The final pellet was resuspended in 50 mM Tris-HCl (pH 7.5) containing 5.68 mM L-ascorbic acid and 5 mM EDTA (equivalent to 12.5 mg wet weight of tissue/ml) and used immediately in the binding assay. Aliquots (400 µl; equivalent to 5 mg wet weight of tissue/tube) of this suspension were added to tubes containing the ligand (50 µl; 1 nM) and distilled water (50 µl; total binding) or phentolamine (50 µl; 5 µM; non-specific binding) or test compound (50 µl; at a single concentration of $10^{-6}$M or at 10 concentrations ranging from $10^{-11}$–$10^{-3}$ M). The ligand was tritiated idazoxan ((1,4-[6,7(n)-$^3$H]benzodioxan-2-yl)-2-imidazoline hydrochloride) and the mixture was incubated at 0° C. for 75 minutes before the incubation was terminated by rapid filtration.

The filters were washed with ice-cold Tris-HCl buffer and dried. The filters were punched out into vials, scintillation fluid added and radioactivity determined by liquid scintillation counting. The percentage displacement of specific binding of the tritiated ligand was calculated for the single concentration ($10^{-4}$M) of test compound. Displacement curves were then produced for those compounds which displaced $\geq 50\%$ of specific binding of the tritiated ligand at $10^{-6}$ M using a range of concentrations of the compound. The concentration which gave 50% inhibition of specific binding ($IC_{50}$) was obtained from the curve. The inhibition coefficient $K_i$ was then calculated using the formula $$K_i = \frac{IC_{50}}{1 + ([\text{ligand}]/K_D)}$$

in which [ligand] is the concentration of the tritiated ligand used and $K_D$ is the equilibrium dissociation constant for the ligand.

The ability of compounds of formula I to interact with dopamine receptors has been demonstrated by the following test which determines the ability of the compounds to inhibit tritiated ligand binding to dopamine receptors in vitro and in particular to the D2 dopamine receptors.

Striatal tissue from the brains of male Charles River CD rats weighing between 140–250 g were homogenised in ice-cold 50 mM Tris-HCl buffer (pH 7.7 when measured at 25° C.) and centrifuged at 40,000 g for 10 minutes. The pellet was resuspended in Tris salts buffer (50 mM Tris-HCl buffer containing 120 mM NaCl, 5 mM KCl, 2 mM $CaCl_2$ and 1 mM $MgCl_2$ with the addition of 6 mM ascorbic acid; pH 7.7 when measured at 25° C.), and again centrifuged at 40,000 g for 10 minutes. The final pellet was stored at −80° C. Before each test the pellet was resuspended in Tris salts buffer (equivalent to 2 mg wet weight of tissue/ml). Aliquots (720 μl; equivalent to 1.44 mg wet weight of tissue/tube) of this suspension were then added to tubes containing the ligand (40 μl; 1 nM) and Tris salts buffer (40 μl; total binding) or spiroperidol (40 μl; 10 nM; non-specific binding) or test compound (40 μl; at a single concentration of $10^{-6}$M or at 6 concentrations ranging from $10^{-11}$–$10^{-4}$M). The ligand was tritiated (S)-sulpiride and the mixture was incubated at 4° C. for 40 minutes before the incubation was terminated by rapid filtration.

The filters were washed with ice-cold Tris-HCl buffer and dried. The filters were punched out in to vials, scintillation fluid added and were left for about 20 hours before being counted by scintillation spectrophotometry. The percentage displacement of specific binding of the tritiated ligand was calculated for the single concentration ($10^{-6}$M) of test compound. Displacement curves were then produced over a range of concentrations for those compounds which displaced ≧50% of specific binding of the tritiated ligand at $10^{-6}$M. The concentration which gave a 50% inhibition of specific binding ($IC_{50}$) was obtained from the curve. The inhibition coefficient $K_i$ was then calculated using the formula $$K_i = \frac{IC_{50}}{1 + ([\text{ligand}]/K_D)}$$

in [ligand] is the concentration of the tritiated ligand used and $K_D$ is the 2 equilibrium dissociation constant for the ligand.

The $K_i$ values obtained in the above tests for 5-$HT_{1A}$, $\alpha_1$, $\alpha_{2A}$, $\alpha_{2D}$ and $D_2$ binding for each of the final products of Examples 1 to 52 hereinafter are given in Table I below.

TABLE 1

| Example Number | Ki (nM) value for | | | | |
|---|---|---|---|---|---|
| | 5-$HT_{1A}$ | $\alpha_{2A}$ | $\alpha_{2D}$ | $D_2$ | $\alpha_1$ |
| 1 | 41.5 | NT | 97% | 32.2 | 89% |
| 2 | 97% | NT | 98% | 104% | 100% |
| 3 | 18 | NT | 99% | 32.9 | 5.3 |
| 4 | 90% | NT | 98% | 84% | 89% |
| 5 | 94 | 98% | 96% | 55.6 | 65 |
| 6 | 27 | 100% | 4.4 | 67 | 21 |
| 7 | 38 | 2.8 | 3.6 | 197 | 104 |
| 8 | 12 | 99% | 100% | 95 | 8 |
| 9 | 54 | 99% | 97% | 37 | 20 |
| 10 | 57 | 100% | 6.4 | 109 | 140 |
| 11 | 19 | 99% | 98% | 41 | 18 |
| 12 | 16 | 99% | 95% | 21 | 132 |
| 13 | 38 | 100% | 99% | 33 | 10 |
| 14 | 26 | NT | 97% | 43.9 | 75 |
| 15 | 40.8 | 100% | 99% | 64.6 | 17 |
| 16 | 63 | 100% | 99% | 68 | 2 |
| 17 | 32 | 99% | 27 | 36 | 70 |
| 18 | 83 | NT | 89% | 110 | 298 |
| 19 | 30 | NT | NT | 11.4 | 49 |
| 20 | 41 | 101% | 98% | 12 | 4 |
| 21 | 35 | NT | NT | 18 | 99 |
| 22 | 35 | 99% | 99% | 15 | 172 |

TABLE 1-continued

| Example Number | Ki (nM) value for | | | | |
|---|---|---|---|---|---|
| | 5-$HT_{1A}$ | $\alpha_{2A}$ | $\alpha_{2D}$ | $D_2$ | $\alpha_1$ |
| 23 | 70 | 98% | 95% | 80 | 44 |
| 24 | 34 | NT | NT | 16 | 9 |
| 25 | 47 | NT | NT | 33 | 233 |
| 26 | 7 | NT | NT | 43 | 130 |
| 27 | 90% | NT | NT | 99.9% | 68% |
| 28 | 96% | NT | NT | 100.9% | 98% |
| 29 | 95% | NT | NT | 101.9 | 85% |
| 30 | 78% | NT | NT | 85% | 61% |
| 31 | 63% | NT | NT | 68% | 41% |
| 32 | 92% | NT | NT | 80% | 71% |
| 33 | 81% | NT | NT | 81% | 41% |
| 34 | 87% | NT | NT | 86% | 68% |
| 35 | 95% | NT | NT | 101% | 73% |
| 36 | 80% | NT | NT | 98% | 54% |
| 37 | 85% | NT | NT | 97% | 66% |
| 38 | 88% | NT | NT | 99% | 51% |
| 39 | 85% | NT | NT | 87% | 43% |
| 40 | 87% | NT | NT | 91% | 60% |
| 41 | 68% | NT | NT | 70% | 29% |
| 42 | 92% | NT | NT | 91% | 62% |
| 43 | 76% | NT | NT | 68% | 59% |
| 44 | 64% | NT | NT | 57% | 38% |
| 45 | 80% | NT | NT | 97% | 94% |
| 46 | 86% | NT | NT | 104% | 98% |
| 47 | 75% | NT | NT | 100% | 94% |
| 48 | 80% | NT | NT | 101% | 93% |
| 49 | 88% | NT | NT | 99% | 93% |
| 50 | 97% | NT | NT | 101% | 98% |
| 51 | 95% | NT | NT | 101% | 98% |
| 52 | 95% | NT | NT | 101% | 97% |

The % figures in Table 1 are for % displacement of the appropriate radio ligand at $10^{-6}$M.
NT means Not Tested The invention is illustrated by the following Examples which are given by way of example only. The final product of each of these Examples was characterised by one or more of the following procedures: gas-liquid chromatography; high performance liquid chromatography; elemental analysis, nuclear magnetic resonance spectroscopy and infrared spectroscopy.

EXAMPLE 1

A mixture of (R)-glycidyl 4-toluenesulphonate (10.0 g), 5-chloro-2-hydroxybenzaldehyde (8.92 g) and potassium carbonate (7.87 g) in dimethylformamide (200 ml) was stirred and heated at 60° C. for 5 hours then allowed to stand for 18 hours. Water (200 ml) was added and the resultant mixture extracted with ether (3×150 ml). The combined ether extracts were washed with brine (3×150 ml), dried over magnesium sulphate and the solvent evaporated. The oily residue was purified by flash chromatography on silica eluting with a 25:1 followed by a 10:1 mixture of petroleum ether (b.p. 40–60° C.) and ethyl acetate to give (R)-5-chloro-2-(2,3-epoxypropoxy)benzaldehyde (8.1 g) contaminated with ~10% of an unknown impurity, which was used without further purification.

A mixture of the product from the previous reaction (8.1 g) and 3-chloroperoxybenzoic acid (85%; 9.2 g) in dichloromethane (100 ml) was heated under reflux for 20 hours then cooled in ice water. The precipitate was filtered and the filtrate washed with saturated aqueous sodium metabisulphite solution (100 ml), saturated aqueous sodium bicarbonate solution (2×100 ml) and brine (100 ml), then dried over magnesium sulphate. The solvent was evaporated to give (R)-5-chloro-2-(2,3-epoxypropoxy)phenyl formate (7.98 g), containing ~10% of an unidentified impurity, as an orange oil, which was used without further purification.

Sodium metal (0.25 g) was dissolved in methanol (20 ml) under nitrogen and a solution of the product from the previous reaction (2.0 g) in methanol (30 ml) was added dropwise. The resultant mixture was stirred for 1 hour then heated under reflux for 2 hours and allowed to stand at ambient temperature for 18 hours. The solvent was removed in vacuo and the residue partitioned between ether (100 ml) and water (100 ml). The ether layer was washed with water (100 ml) and dried over magnesium sulphate. The solvent was evaporated to give (S)-7-chloro-1,4-benzodioxan-2-ylmethanol as a yellow oil (1.67 g)

4-Toluenesulphonyl chloride (5.9 g) was added to a solution of (S)-7-chloro-1,4-benzodioxan-2-ylmethanol (6.0 g; prepared by the method described above) in pyridine (40 ml) and the mixture stirred for 4 hours. More 4-toluenesulphonyl chloride (250 mg) was added, stirring continued for 2 hours, then further 4-toluenesulphonyl chloride (250 mg) was added and stirring continued for 1 hour. The mixture was poured into water (200 ml) and extracted with ethyl acetate (2×200 ml). The combined extracts were washed with hydrochloric acid (2M; 2×200 ml), saturated aqueous sodium bicarbonate solution (2×200 ml) and brine (200 ml), then dried over magnesium sulphate. The solvent was removed in vacuo and the residue recrystallised from ether to give (R)-7-chloro-1,4-benzodioxan-2-ylmethyl 4-toluenesulphonate (7.00 g) m.p. 90–91° C.

A mixture of 5-bromo-2-hydroxybenzaldehyde (170 g) and 4-(aminomethyl)piperidine (96.9 g) in ethanol (2.5 L) was stirred at ambient temperature for 3 hours. The solvent was removed in vacuo to give 4-bromo-2-[N-(4-piperidylmethyl)iminomethyl]phenol (267 g) as a yellow solid m.p 35–38° C.

A mixture of the product from the previous reaction (6.87 g), (R)-7-chloro-1,4-benzodioxan-2-ylmethyl 4-toluenesulphonate (4.1 g) and potassium carbonate (1.6 g) in acetonitrile (160 ml) was heated under reflux for 18 hours. After cooling and filtering the solvent was removed in vacuo and the residue purified by flash chromatography on silica eluting with a 1:2 mixture of ethyl acetate and petroleum ether (b.p. 60–80° C.) followed by neat ethyl acetate. Appropriate fractions were combined and the solvent removed in vacuo to give (S)-4-bromo-2-{N-[1-(7-chloro-1,4-benzodioxan-2-ylmethyl)piperid-4-ylmethyl]iminomethyl}phenol (4.0 g) as a yellow oil.

The product from the previous reaction (4.0 g) in a mixture of aqueous potassium hydrogen sulphate solution (1M; 30 ml) and industrial methylated spirit (5 ml) was heated to 70° C. for 5 minutes then stirred at ambient temperature for 1 hour. The mixture was washed with ether (3×50 ml) then saturated aqueous sodium carbonate solution was added to give pH 11. The mixture was extracted with dichloromethane (3×50 ml), the combined extracts dried over magnesium sulphate and the solvent evaporated to give (S)-4-(aminomethyl)-1-(7-chloro-1,4-benzodioxan-2-ylmethyl)piperidine (1.94 g) as a colourless oil.

A mixture of the product from the previous reaction (1.0 g) and pyrido[2,3-d][1,3]oxazine-2,4-(1H)-dione (0.55 g) in 1,2-dimethoxyethane (30 ml) was heated under reflux for 16 hours. The solvent was removed in vacuo and the residue purified by flash chromatography on silica eluting with a 97:3 followed by a 95:5 mixture of dichloromethane and methanol. Appropriate fractions were combined and the solvent was removed in vacuo. The residue was triturated with ether to give (S)-(−)-2-amino-N-{[1-(7-chloro-1,4-benzodioxan-2-ylmethyl)-4-piperidyl]methyl}pyridine-3-carboxamide (0.80 g) m.p. 150–152° C., $[\alpha]_D$ −50.65° (c=0.918, MeOH)

EXAMPLE 2

A stirred mixture of 2-chloro-6-hydroxybenzaldehyde (4.4 g), (R)-glycidyl 4-toluenesulphonate (5.0 g) and potassium carbonate (3.9 g) in dimethylformamide (120 ml) was heated at 60° C. for 5 hours then allowed to stand at ambient temperature for 18 hours. The solvent was removed in vacuo, water (60 ml) was added and the mixture extracted with ether (3×100 ml). The combined extracts were dried over magnesium sulphate and the solvent evaporated. The residue was purified by flash chromatography on silica eluting with a 1:1 mixture of petroleum ether (b.p. 60–80° C.) and dichloromethane followed by a 19:1 mixture of dichloromethane and industrial methylated spirit. Appropriate fractions were combined and the solvent was removed in vacuo to give (R)-2-chloro-6-(2,3-epoxypropoxy) benzaldehyde (2.8 g) m.p. 62–64° C.

A solution of the product from the previous reaction (2.8 g) and 3-chloroperoxybenzoic acid (85%; 4.8 g) in dichloromethane (200 ml) was heated under reflux for 18 hours. More 3-chloroperoxybenzoic acid (4.8 g) was added and reflux continued for 6 hours. The mixture was washed with saturated aqueous sodium bicarbonate solution (3×200 ml) then dried over magnesium sulphate. The solvent was removed in vacuo to give (R)-2-chloro-6-(2,3-epoxypropoxy)phenyl formate (2.8 g) as a yellow solid.

A stirred solution of the product from the previous reaction (2.8 g) in aqueous sodium hydroxide soution (2.5 M; 20 ml) was heated under reflux for 1.5 hours. The cooled solution was extracted with dichloromethane (2×30 ml), the combined extracts dried over magnesium sulphate and the solvent was removed in vacuo to give (S)-8-chloro-1,4-benzodioxan-2-ylmethanol (1.63 g) as a yellow oil.

A solution of 4-toluenesulphonyl chloride (1.7 g) in pyridine (10 ml) was added dropwise to a solution of the product of the previous reaction (1.63 g) in pyridine (30 ml) and the mixture stirred at ambient temperature for 4 hours then warmed to 50° C. for 30 minutes. The cooled solution was poured into hydrochloric acid (5 M; 50 ml) then extracted with dichloromethane (3×50 ml). The combined extracts were dried over magnesium sulphate and the solvent was removed in vacuo to give (R)-8-chloro-1,4-benzodioxan-2-ylmethyl 4-toluenesulphonate as an orange oil (2.33 g).

A mixture of 4-(aminomethyl)-1-(tert-butoxycarbonyl) piperidine (2.0 g) and pyrido[2,3d][1,3]oxazine-2,4-(1H)-dione (1.53 g) in 1,2-dimethoxyethane (30 ml) was stirred at ambient temperature for 3 hours. The solvent was removed in vacuo and the residue purified by flash chromatography on silica eluting with dichloromethane then a 19:1 mixture fo dichloromethane and industrial methylated spirit. Appropriate fractions were combined and the solvent was removed in vacuo to give 2-amino-N-[(1-tert-butoxycarbonyl-4-piperidyl)methyl]pyridine-3-carboxamide (1.7 g).

Trifluoroacetic acid (9 ml) was added to a solution of 2-amino-N-[(1-tert-butoxycarbonyl-4-piperidyl)methyl] pyridine-3-carboxamide (2.2 g; prepared in a similar manner to that described above) in dichloromethane (50 ml) and the mixture stirred at ambient temperature for 1 hour. The solvent was removed in vacuo to give crude 2-amino-N-(4-piperidylmethyl)pyridine-3-carboxamide trifluoroacetate.

A mixture of this material, (R)-8-chloro-1,4-benzodioxan-2-ylmethyl 4-toluenesulphonate (2.3 g) and potassium carbonate (3.6 g) in acetonitrile (70 ml) was heated under reflux for 6 hours. The solvent was removed in vacuo, water (50 ml) added to the residue and the mixture extracted with dichloromethane (2×30 ml). The combined organics were extracted with hydrochloric acid (2.5 M; 2×30 ml) then the combined extracts were basified with aqueous sodium hydroxide solution (5 M) and extracted with dichloromethane (2×30 ml). The combined organics were dried over magnesium sulphate and the solvent was removed in vacuo. The residue was purified by flash chromatography on silica eluting with a 9:1 mixture of dichloromethane and methanol. Appropriate fractions were combined and the solvent was removed in vacuo to give (S)-2-amino-N-{[1-(8-chloro-1,4-benzodioxan-2-ylmethyl)-4-piperidyl]methyl}-pyridine-3-carboxamide (1.0 g) m.p. 62–70° C., $[\alpha]_D$ –35.47° (c=0.888, MeOH).

EXAMPLE 3

A solution of butyllithium in hexanes (2.5 M; 15.9 ml) was added to a stirring solution of 3-fluoroanisole (5.0 g) in dry tetrahydrofuran (100 ml) at –78° C. and the mixture stirred at that temperature for 30 min. Dry dimethylformamide (3.1 ml) was added and the mixture stirred and allowed to warm to ambient temperature during one hour. Water (150 ml) was added and the mixture extracted with ethyl acetate (3×100 ml). The combined extracts were washed with brine (100 ml), dried over magnesium sulphate, and the solvent removed in vacuo. Distillation of the residue under reduced pressure gave 2-fluoro-6-methoxybenzaldehyde (4.6 g) as an oil b.p. 120° C. at 10.66 mbar.

A solution of boron tribromide in dichloromethane (1M; 20.15 ml) was added dropwise to a stirring solution of 2-fluoro-6-methoxybenzaldehyde (4.66 g, prepared as described above) in dichloromethane (40 ml) at –78° C. The mixture was allowed to warm to ambient temperature then water (150 ml) was added and the mixture extracted with dichloromethane (3×100 ml). The combined extracts were washed with water (100 ml) then brine (100 ml) and the solvent evaporated. Distillation of the residue at reduced pressure gave 2-fluoro-6-hydroxybenzaldehyde (2.0 g), contaminated with 7% of the starting methoxy compound, as an oil b.p. 60° C. at 4.66 mbar, which was used without further purification.

A mixture of the product from the previous reaction (1.7 g), (R)-glycidyl 4-toluenesulphonate (2.1 g) and potassium carbonate (1.68 g) in dimethylformamide (50 ml) was stirred and heated at 60° C. for 5 hours. After stirring at ambient temperature for 18 hours the mixture was poured into water (150 ml) then extracted with ethyl acetate (3×100 ml). The combined extracts were washed with brine (100 ml) and dried over magnesium sulphate. The solvent was removed in vacuo and the oily residue passed through a pad of silica gel eluting with a 1:2 mixture of ethyl acetate and petroleum ether (b.p. 60–80° C.). The solvent was removed in vacuo to give (R)-2-(2,3-epoxypropoxy)-6-fluorobenzaldehyde (0.71 g) as an oil.

A mixture of the product from the previous reaction (0.71 g) and 3-chloroperoxybenzoic acid (85%; 0.87 g) in dichloromethane (100 ml) was heated under reflux for 3 days. Further 3-chloroperoxybenzoic acid (0.87 g) was added and reflux continued for 18 hours. The mixture was poured into saturated aqueous sodium carbonate solution (250 ml) and extracted with dichloromethane (3×100 ml). The combined extracts were washed with brine (100 ml) then dried over magnesium sulphate and the solvent evaporated in vacuo to give (R)-2-(2,3-epoxypropoxy)-6-fluorophenyl formate (0.34 g) as an oil.

Sodium metal (0.89 g) was dissolved in methanol (100 ml) and a solution of (R)-2-(2,3-epoxypropoxy)-6-fluorophenyl formate (6.56 g, prepared as described above) in methanol (100 ml) added dropwise. The mixture was stirred for one hour at ambient temperature then heated under reflux for two hours, allowed to stand for 3 days, and then heated under reflux for 4 hours. The solvent was removed in vacuo, water (100 ml) was added and the mixture extracted with ethyl acetate (4×100 ml). The combined extracts were washed with brine (100 ml), dried over magnesium sulphate and the solvent evaporated in vacuo to give crude (S)-8-fluoro-1,4-benzodioxan-2-ylmethanol (3.85 g) which was used without further purification.

4-Toluenesulphonyl chloride (4.1 g) was added to a solution of the crude product from the previous reaction (3.85 g) in pyridine (50 ml) and the mixture stirred for 18 hours before pouring into hydrochloric acid (5M; 100 ml). The mixture was extracted with ethyl acetate (3×100 ml) and the combined extracts washed with brine (100 ml) then dried over magnesium sulphate. The solvent was removed in vacuo to give crude (R)-8-fluoro-1,4-benzodioxan-2-ylmethyl 4-toluenesulphonate (4.1 g) as a semi-solid, which was used without further purification.

A mixture of crude 2-amino-N-(4-piperidylmethyl)pyridine-3-carboxamide (7.21 g; prepared in a similar manner to that described in Example 2), potassium carbonate (4.15 g) and (R)-8-fluoro-1,4-benzodioxan-2-ylmethyl toluene-4-sulphonate (2 g) in acetonitrile (100 ml) was heated under reflux for 16 hours. After cooling and filtering the solvent was removed in vacuo and the residue purified by chromatography on silica eluting with neat ethyl acetate. Appropriate fractions were combined and the solvent removed in vacuo to give a solid (1.5 g). This solid (0.78 g) was dried in vacuo and ground to give (S)-(–)-2-amino-N-{[1-(8-fluoro-1,4-benzodioxan-2-ylmethyl)-4-piperidyl]methyl}pyridine-3-carboxamide 0.5 hydrate 0.15 ethyl acetate, solvate (610 mg) m.p. 115–116° C., $[\alpha]_D$ –39.09° (c=0.967, methanol).

EXAMPLE 4

A stirred mixture of 1,4-benzodioxan-2-ylmethyl toluene4-sulphonate (0.82 g), 2-amino-N-(4-piperidylmethyl)pyridine-3-carboxamide trifluoroacetate (0.905 g; prepared in a similar manner to that described in Example 2) and potassium carbonate (1.4 g) in acetonitrile (50 ml) was heated under reflux for 6 hours. After cooling, the solvent was removed in vacuo, water (60 ml) was added to the residue, and the product was extracted with dichloromethane (2×30 ml). The extracts were dried over magnesium sulphate and the solvent was removed in vacuo to give an oil. The oil was purified by flash chromatography on silica eluting with a 9:1 then 1:1 mixture of dichloromethane and methanol. Appropriate fractions were combined and the solvents removed in vacuo to give an oil. Ethereal maleic acid (20 ml) was added to yield a white solid. The solid was collected by filtration, washed with ether and the solvent removed in vacuo to yield 2-amino-N-{[1-(1,4-benzodioxan-2-ylmethyl)-4-piperidyl]methyl}pyridine-3-carboxamide 0.5 maleate (95 mg) m.p. 104–106° C.

EXAMPLE 5

A mixture of 2-hydroxy-5-methylbenzaldehyde (7.1 g), (R)-glycidyl 4-toluenesulphonate (11.9 g) and potassium carbonate (7.25 g) in anhydrous 1,2-dimethoxyethane (150 ml) was stirred and heated at 60° C. for 5 hours, allowed to stand at ambient temperature for 18 hours, heated at 60° C.

for a further 8 hours then allowed to cool for 18 hours. The solvent was removed in vacuo and the residue partitioned between water (250 ml) and ether (250 ml). The mixture was filtered through Celite, the ether layer separated, washed with water and dried over magnesium sulphate. The solvent was evaporated and the residue purified by flash chromatography on silica eluting with a 1:1 mixture of ether and petroleum ether (b.p. 40–60° C.). Appropriate fractions were combined and the solvent evaporated to give (R)-2-(2,3-epoxypropoxy)-5-methylbenzaldehyde (8.91 g) as an oil.

A solution of the product from the previous reaction (8.91 g) and 3-chloroperoxybenzoic acid (86%; 19.6 g) in dichloromethane (250 ml) was stirred at ambient temperature for 18 hours. The solution was washed with dilute sodium hydrogen carbonate solution (2×200 ml) then water (150 ml) and dried over magnesium sulphate. The solvent was evaporated and the resultant crude (R)-2-(2,3-epoxypropoxy)-5-methylphenyl formate (14.0 g), which still contained some 3-chlorobenzoic acid, was used without further purification.

The crude product from the previous reaction (14.0 g) was dissolved in aqueous sodium hydroxide solution (2.5 M; 100 ml) and the mixture stirred and heated at 95–100° C. for 1½ hours. The cooled solution was extracted with dichloromethane (2×200 ml), the combined extracts dried over magnesium sulphate and the solvent evaporated. The residue was purified by chromatography on silica, eluting with a 1:1 mixture of ether and petroleum ether (b.p. 40–60° C. ). Appropriate fractions were combined and the solvent evaporated to give (S)-7-methyl-1,4-benzodioxan-2-ylmethanol (4.71 g) as an oil.

A solution of 4-toluenesulphonyl chloride (5.5 g) in anhydrous pyridine (50 ml) was added dropwise to a solution of the product from the previous reaction (4.7 g) in anhydrous pyridine (50 ml) and the mixture stirred at ambient temperature for two hours then at 50° C. for 2 hours. The mixture was poured onto ice, acidified with hydrochloric acid (5M), then extracted with dichloromethane (2×200 ml). The combined extracts were washed with saturated brine then dried over magnesium sulphate. The solvent was evaporated and the residue purified by chromatography on silica, eluting with a 1:1 mixture of ether and petroleum ether (b.p. 40–60° C.). Appropriate fractions were combined and the solvent evaporated to give (R)-7-methyl-1,4-benzodioxan-2-ylmethyl 4-toluenesulphonate (4.53 g) as a solid.

Trifluoroacetic acid (5 ml) was added to a solution of 2-amino-N-[(1-tert-butoxycarbonyl-4-piperidyl)methyl]pyridine-3-carboxamide (0.92 g; prepared in a similar manner to that described in Example 2) in dichloromethane (10 ml) then the mixture stirred at ambient temperature for 2 hours and the solvent removed in vacuo. The crude 2-amino-N-(4-piperidylmethyl)pyridine-3-carboxamide trifluoroacetate thus produced was dissolved in anhydrous acetonitrile (10 ml) and potassium carbonate (1.5 g) was added, followed by a solution of (R)-7-methyl-1,4-benzodioxan-2-ylmethyl 4-toluenesulphonate (0.9 g) in anhydrous acetonitrile (5 ml). The mixture was heated under reflux for 18 hours then poured onto water and extracted with ether (2×100 ml). The combined extracts were washed with water then extracted with hydrochloric acid (1M; 50 ml). The acid extracts were washed with ether (100 ml) then basified with sodium hydrogen carbonate and extracted with ether (2×100 ml). These extracts were combined, washed with water and dried over magnesium sulphate. The solvent was evaporated and the residue purified by flash chromatography on silica eluting with a 20:1 mixture of dichloromethane and methanol. Appropriate fractions were combined and evaporated to give (S)-2-amino-N-{[1-(7-methyl-1,4-benzodioxan-2-ylmethyl)-4-piperidyl]methyl}pyridine-3-carboxamide as a colourless solid (0.36 g) m.p. 143–146° C., $[\alpha]_D$ −46.23° (c=0.53, methanol).

EXAMPLE 6

A mixture of pyridine-2-carboxylic acid (2.7 g) and 4-(aminomethyl)-1-tert-butoxycarbonylpiperidine (5.0 g) in dry xylene (50 ml) was heated under reflux under a Dean and Stark water separator for six hours. The cooled solution was diluted with ethyl acetate (150 ml), washed with aqueous oxalic acid solution (2M; 2×100 ml) then aqueous sodium hydrogen carbonate soultion (5M; 2×100 ml) and dried over magnesium sulphate. The solvent was removed in vacuo to give N-[(1-tert-butoxycarbonyl-4-piperidyl)methyl]pyridine-2-carboxamide (2.53 g) as an oil.

Trifluoroacetic acid (16 ml) was added to a solution of the product from the previous reaction (2.5 g) in dichloromethane (50 ml) and the mixture stirred at ambient temperature for 2 hours. The solvents were removed in vacuo and the residue dissolved in dry acetonitrile (25 ml). Potassium carbonate (7.0 g) and 1,4-benzodioxan-2-ylmethyl 4-toluenesulphonate (2.4 g) were added and the mixture heated under reflux for 18 hours, then cooled and poured into water. The resultant mixture was extracted with dichloromethane (2×100 ml) and the combined extracts washed with water then dried over magnesium sulphate. The solvent was evaporated and the residue purified by flash chromatography over silica eluting with ethyl acetate. Appropriate fractions were combined and the solvent removed in vacuo to give N-{[1-(1,4-benzodioxan-2-ylmethyl)-4-piperidyl]methyl}pyridine-2-carboxamide (2.43 g) as a colourless solid m.p. 95–97° C.

EXAMPLE 7

A mixture of 2-hydroxy-5-methoxybenzaldehyde (6.65 g), (R)-glycidyl 4-toluenesulphonate (10.0 g) and potassium carbonate (6.1 g) in dry dimethylformamide (100 ml) was stirred and heated at 60° C. for five hours. The solvent was removed in vacuo, water was added to the residue and the mixture extracted with ether (2×200 ml). The combined extracts were washed with water and dried over magnesium sulphate. The solvent was evaporated and the residue purified by flash chromatography over silica eluting with a 2:1 mixture of ether and petroleum ether (b.p. 40–60° C.). Appropriate fractions were combined and the solvent evaporated to give (R)-2-(2,3-epoxypropoxy)-5-methoxybenzaldehyde (7.25 g) as a clear oil.

A solution of the product from the previous reaction (7.25 g) and 3-chloroperoxybenzoic acid (86%, 14.85 g) in dichloromethane (200 ml) was stirred at ambient temperature for 20 hours. Water (200 ml) was added, the organic layer separated, washed with sodium hydrogen carbonate solution (5M; 3×200 ml) then with water, and dried over magnesium sulphate. The solvent was evaporated to give (R)-2-(2,3-epoxypropoxy)-5-methoxyphenyl formate (7.1 g) as a clear oil.

A solution of the product from the previous reaction (7.1 g) in aqueous sodium hydroxide solution (2.5 M; 100 ml) was heated at 95–100° C. for 1½ hours. The cooled mixture was extracted with ether (2×200 ml) and the combined extracts dried over magnesium sulphate. The solvent was evaporated to give (S)-7-methoxy-1,4-benzodioxan-2-ylmethanol (3.64 g) as a solid.

A solution of 4-toluenesulphonyl chloride (3.54 g) in dry pyridine (35 ml) was added to a solution of the product from the previous reaction (3.64 g) in dry pyridine (60 ml) and the mixture stirred at ambient temperature for 18 hours, then poured onto ice. The mixture was acidified with hydrochloric acid (5 M) then extracted with dichloromethane (200 ml). The combined extracts were dried over magnesium sulphate and the solvent was evaporated to give (R)-7-methoxy-1,4-benzodioxan-2-ylmethyl 4-toluenesulphonate (5.1 g) as a colourless solid.

Trifluoroacetic acid (10 ml) was added to a solution of 2-amino-N-[(1-tert-butoxycarbonyl-4-piperidyl)methyl] pyridine-3-carboxamide (2.5 g; prepared in a similar manner to that described in Example 2) in dichloromethane (10 ml) then the mixture stirred at ambient temperature for 2 hours and the solvent removed in vacuo. The residue was dissolved in acetonitrile (75 ml) then potassium carbonate (15 g) and the product from the previous reaction (2.5 g) were added and the mixture heated under reflux for 20 hours. The cooled mixture was poured onto water (200 ml) then extracted with dichloromethane (2×200 ml). The combined extracts were dried over magnesium sulphate, the solvent was evaporated and the residue purified by chromatography over silica eluting with ethyl acetate followed by a 9:1 mixture of ethyl acetate and methanol. Appropriate fractions were combined and the solvent removed in vacuo. The residue was recrystallised from ethyl acetate to give (S)-2-amino-N{[1-(7-methoxy-1,4-benzodioxan-2-ylmethyl)-4-piperidyl]methyl}-pyridine-3-carboxamide (1.15 g) m.p. 156–158° C. $[\alpha]_D$ –46.5° (c=0.505, methanol).

EXAMPLE 8

Quinoline-8-carboxylic acid (0.74 g) and thionyl chloride (10 ml) were stirred and heated together at 50° C. for 2 hours. Excess thionyl chloride was removed in vacuo and the residue was suspended in dichloromethane (20 ml). A solution of 4-(aminomethyl)-1-tert-butoxycarbonylpiperidine (0.98 g) in dichloromethane (10 ml) was added and the mixture stirred at ambient temperature for 4 hours then poured into aqueous sodium hydrogen carbonate solution (1M; 50 ml). The organic layer was separated and washed with aqueous oxalic acid solution (2M; 2×50 ml) then dried over magnesium sulphate. The solvent was evaporated to give N-[(1-tert-butoxycarbonyl-4-piperidyl)methyl]quinoline-8-carboxamide (0.59 g) as a colourless solid.

Trifluoroacetic acid (5 ml) was added to a solution of N-[(1-tert-butoxycarbonyl-4-piperidyl)methyl]quinoline-8-carboxamide (1.11 g; prepared in a similar manner to that described above) in dichloromethane (20 ml) and the mixture heated under reflux for 2 hours then cooled and the solvents removed in vacuo. The residue was dissolved in dry acetonitrile (50 ml), potassium carbonate (3.0 g) and 1,4-benzodioxan-2-ylmethyl 4-toluenesulphonate (0.92 g) were added and the mixture stirred and heated under reflux for 20 hours. The cooled mixture was poured onto water (100 ml) and extracted with dichloromethane (2×100 ml). The combined extracts were washed with water and dried over magnesium sulphate. The solvent was evaporated and the residue was purified by flash chromatography over silica eluting with ethyl acetate. Appropriate fractions were combined and the solvent removed in vacuo to leave an oil which was dissolved in methanol (10 ml) and fumaric acid (0.4 g) was added. The solvent was removed in vacuo to give N-{[1-(1,4-benzodioxan-2-ylmethyl)-4-piperidyl]methyl}quinoline-8-carboxamide 2.5 fumarate (1.12 g) m.p. 117–120° C. (softens at 78° C.).

EXAMPLE 9

A mixture of 2-chloro-6-hydroxybenzaldehyde (4.4 g), (R)-glycidyl 4-toluenesulphonate (5.0 g) and potassium carbonate (3.9 g) in dimethylformamide (120 ml) was stirred and heated at 60° C. for 5 hours and allowed to cool over 18 hours. The solvent was removed in vacuo, water (60 ml) was added to the residue and the mixture extracted with ether (3×100 ml). The combined extracts were dried over magnesium sulphate and the solvent was evaporated. The residual oil was purified by flash chromatography on silica eluting with a 1:1 mixture of petroleum ether (b.p. 40–60° C.) and dichloromethane, followed by neat dichloromethane then a 19:1 mixture of dichloromethane and industrial methylated spirit. Appropriate fractions were combined and the solvent removed in vacuo to give (R)-2-chloro-6-(2,3-epoxypropoxy)benzaldehyde as a pale yellow solid (2.8 g). Other, incompletely purified, fractions gave material which was subjected to repeat chromatography, providing a second crop of product (0.5 g).

A solution of the product from the previous reaction (2.8 g) and 3-chloroperoxybenzoic acid (86%, 4.8 g) in dichloromethane (200 ml) was stirred and heated under reflux for 18 hours. More 3-chloroperoxybenzoic acid (86%; 4.8 g) was added and the solution heated under reflux for 6 hours. The mixture was washed with saturated aqueous sodium hydrogen carbonate solution (3×200 ml), dried over magnesium sulphate and the solvent was evaporated to give (R)-2-chloro-6-(2,3-epoxypropoxy)phenyl formate (2.8 g) as a yellow solid.

A solution of the product from the previous reaction (2.8 g) in aqueous sodium hydroxide solution (2.5 M; 20 ml) was stirred and heated under reflux for 1½ hours. The cooled solution was extracted with dichloromethane (2×30 ml), the combined extracts dried over magnesium sulphate, and the solvent evaporated to give (S)-8-chloro-1,4-benzodioxan-2-ylmethanol (1.63 g) as a yellow oil.

A solution of 4-toluenesulphonyl chloride (3.15 g) in dry pyridine (15 ml) was added to a solution of (S)-8-chloro-1,4-benzodioxan-2-ylmethanol (3.32 g; prepared in a similar manner to that described above) in dry pyridine (40 ml) and the mixture stirred at ambient temperature for 18 hours, then poured onto ice and dilute hydrochloric acid added to give pH4. The mixture was extracted with dichloromethane (2×200 ml) and the combined extracts washed with brine and dried over magnesium sulphate. The solvent was evaporated to give (R)-8-chloro-1,4-benzodioxan-2-ylmethyl 4-toluenesulphonate (5.21 g) as a pale yellow solid.

A mixture of the product from the previous reaction (2.5 g), N-benzylidene-1-(4-piperidyl)methylamine (1.42 g) and potassium carbonate (2.0 g) in dry acetonitrile (50 ml) was stirred and heated under reflux for 24 hours. The cooled mixture was poured into water (100 ml) then extracted with dichloromethane (2×100 ml). The combined extracts were washed with brine then dried over magnesium sulphate.The solvent was evaporated and the residue separated from polar material by passage through a silica pad, eluting with ether. The solvent was evaporated to give partially purified (S)-N-benzylidene-1-[1-(8-chloro-1,4-benzodioxan-2-ylmethyl)-4-piperidyl]methylamine (1.72 g) as a cream solid.

The product from the previous reaction (1.7 g) was stirred in an aqueous potassium hydrogen sulphate solution (1M; 100 ml) for two hours at ambient temperature. The solution was washed with ether (100 ml), basified with aqueous sodium hydroxide solution (5M) and extracted with dichloromethane (2×200 ml). The combined extracts were washed with water (100 ml) then dried over magnesium sulphate. The solvent was evaporated to give (S)-4-(aminomethyl)-1-(8-chloro-1,4-benzodioxan-2-ylmethyl)piperidine (0.65 g) as an oil.

Triethylamine (0.22 g), and then ethyl chloroformate (0.24 g), were added to a solution of 2-methylpyridine-3-carboxylic acid (0.3 g) in dichloromethane (20 ml) and the mixture stirred at ambient temperature for 18 hours. A solution of the product of the previous reaction (0.65 g) in dichloromethane (10 ml) was then added dropwise and the mixture stirred at ambient temperature for 24 hours, then washed with water (100 ml) and dried over magnesium sulphate. The solvent was evaporated and the residue purified by flash chromatography over silica eluting with a 15:1 mixture of dichloromethane and methanol. Appropriate fractions were combined and the solvent removed in vacuo giving (S)-N-{[1-(8-chloro-1,4-benzodioxan-2-ylmethyl)-4-piperidyl]methyl}-2-methylpyridine-3-carboxamide (0.37 g) as a solid m.p. 147–149° C., $[\alpha]_D$ –37.9° (c=1.0035, methanol).

EXAMPLE 10

Epichlorohydrin (38 g) was added to a stirred solution of 5'-fluoro-2'-hydroxyacetophenone (20.9 g) in ethanol (20 ml). A solution of potassium hydroxide (9.5 g) in a mixture of ethanol (30 ml) and water (5 ml) was then added and stirring continued for one hour. The solvent was removed in vacuo and the residue poured into water then extracted with ethyl acetate. The combined extracts were washed with brine and dried over magnesium sulphate. The solvent was removed in vacuo and the residue purified by chromatography on silica, eluting with a 9:1 mixture, then a 3:2 mixture, of petroleum ether (b.p. 40–60° C.) and ethyl acetate. Appropriate fractions were combined and the solvent removed in vacuo to give 2'-(2,3-epoxypropoxy)-5'-fluoroacetophenone (4.68 g) as an oil.

A solution of the product from the previous reaction (4.68 g) and 3-chloroperoxybenzoic acid (80%; 5.86 g) in chloroform (50 ml) was heated under reflux for 18 hours. After cooling the mixture was washed with saturated aqueous sodium hydrogen carbonate solution, then brine, and the solvent removed in vacuo to give crude 2-(2,3-epoxypropoxy)-5-fluorophenyl acetate (4.44 g) which was used without further purification.

The crude product from the previous reaction (4.0 g) and aqueous sodium hydroxide solution (10%; 7.3 ml) were heated together under reflux for five hours. The cooled mixture was poured into water and extracted with ethyl acetate. The combined organics were washed with brine then dried over magnesium sulphate. The solvent was removed in vacuo to give 7-fluoro-1,4-benzodioxan-2-ylmethanol (2.0 g).

4-Toluenesulphonyl chloride (2.14 g) was added to a solution of the product from the previous reaction (2.0 g) in pyridine (50 ml) and the mixture stirred at ambient temperature for 18 hours. The mixture was poured into a mixture of ice and dilute hydrochloric acid then extracted with ethyl acetate. The combined organics were washed with brine, dried over magnesium sulphate, and the solvent evaporated to give product contaminated with a considerable amount of starting material. This crude product was reacted with further 4-toluenesulphonyl chloride (2.14 g) in pyridine (50 ml) as above, and worked up as above to give impure product which was purified by flash chromatography on silica eluting with a 20:1 mixture of dichloromethane and methanol. Appropriate fractions were combined and the solvent removed in vacuo to give 7-fluoro-1,4-benzodioxan-2-ylmethyl 4-toluenesulphonate (0.78 g) as a clear oil.

Trifluoroacetic acid (5 ml) was added to a solution of 2-amino-N-[(1-tert-butoxycarbonyl-4-piperidyl)methyl] pyridine-3-carboxamide (0.78 g; prepared in a similar manner to that described in Example 2) in dichloromethane (25 ml) and the mixture stirred at ambient temperature for two hours. The solvent was removed in vacuo and the residue dissolved in acetonitrile (20 ml). To this solution was added potassium carbonate (3.0 g) and a solution of the product from the previous reaction (0.75 g) in acetonitrile (10 ml), then the mixture stirred and heated under reflux for 18 hours. The cooled mixture was filtered and the solid obtained washed with dichloromethane (100 ml). The filtrate and the washings were combined, washed with water (2×100 ml) and dried over magnesium sulphate. The solvent was removed in vacuo and the residue purified by flash chromatography on silica, eluting with a 25:1 mixture of dichloromethane and methanol. Appropriate fractions were combined and the solvent removed in vacuo to give 2-amino-N-{[1-(7-fluoro-1,4-benzodioxan-2-ylmethyl)-4-piperidyl]methyl}pyridine-3-carboxamide (0.56 g) as a colourless solid m.p. 141–143° C.

EXAMPLE 11

Trifluoroacetic acid (10 ml) was added to a solution of 2-amino-N-[(1-tert-butoxycarbonyl-4-piperidyl)methyl] pyridine-3-carboxamide (2.5 g; prepared in a similar manner to that described in Example 2) in dichloromethane (50 ml) and the mixture stirred at ambient temperature for two hours. The solvent was removed in vacuo and the residue dissolved in acetonitrile (50 ml). To this solution was added potassium carbonate (3.0 g) and a solution of 8-methoxy-1,4-benzodioxan-2-ylmethyl 4-toluenesulphonate (2.5 g; prepared in a similar manner to that described in WO95/07274) in acetonitrile (20 ml). The resultant suspension was stirred and heated under reflux for 20 hours, cooled, then poured into water (100 ml) and the mixture extracted with dichloromethane (2×100 ml). The combined extracts were washed with water (100 ml), dried over magnesium sulphate and the solvent was evaporated to give an oil. The product was purified by chromatography over silica using a 9:1 mixture of ethyl acetate and methanol as eluant. Appropriate fractions were combined and the solvent removed in vacuo to give 2-amino-N-{[1-(8-methoxy-1,4-benzodioxan-2-ylmethyl)-4-piperidyl]methyl}pyridine-3-carboxamide 0.4 ethyl acetate solvate 0.5 hydrate as a colourless solid (1.55 g) m.p. 57–60° C.

EXAMPLE 12

Trifluoroacetic acid (25 ml) was added to a solution of N-[(1-tert-butoxycarbonyl-4-piperidyl)methyl]pyridine-2-carboxamide (5.2 g) in dichloromethane (50 ml) and the mixture stirred at ambient temperature for 2 hours. The solvents were removed in vacuo and the residue dissolved in dry acetonitrile (50 ml). Potassium carbonate (25 g) and (R)-7-chloro-1,4-benzodioxan-2-ylmethyl 4-toluenesulphonate (6.0 g; prepared in a similar manner to that described in Example 1) were added and the mixture stirred and heated under reflux for 24 hours. The cooled reaction mixture was filtered and the solvent removed in vacuo. The residue was dissolved in ethyl acetate and the solution washed with water then dried over magnesium sulphate. The solvent was removed in vacuo and the residue purified by flash chromatography on silica, eluting with ethyl acetate followed by a 20:1 mixture of ethyl acetate and methanol. Appropriate fractions were combined and the solvent removed in vacuo to give (S)-N-{[1-(7-chloro-1,4-benzodioxan-2-ylmethyl)-4-piperidyl]methyl}pyridine-2-carboxamide (4.42 g) m.p. 110–112° C. $[\alpha]_D$ 47.7° (c=1.005, methanol)

EXAMPLE 13

A mixture of 2-benzyloxy-3-hydroxybenzaldehyde (60.0 g), (R)-glycidyl 4-toluenesulphonate (60.0 g) and potassium carbonate (74 g) in dry dimethylformamide (600 ml) was stirred and heated at 60° C. for 14 hours. After cooling the solvent was removed in vacuo, water (250 ml) added, and the mixture extracted with ether (2×200 ml), then ethyl acetate (2×400 ml). The combined extracts were washed with brine (2×500 ml) and dried over magnesium sulphate. The solvent was removed in vacuo and the residue purified by flash chromatography on silica, pre-adsorbing onto silica first by evaporation from a solution in dichloromethane, then eluting with a 3:1 mixture of petroleum ether (b.p. 40–60° C.) and ether. Appropriate fractions were combined and the solvent removed in vacuo to give (R)-2-benzyloxy-3-(2,3-epoxypropoxy)benzaldehyde (14.22 g). A further crop of product (33.37 g) was obtained by extraction of the silica employed in the chromatography with ether (6×500 ml), followed by concentration of the combined extracts to a volume of ~500 ml and cooling overnight, filtering, then washing the precipitate with a 1:1 mixture of petroleum ether (b.p. 40–60° C.) and ether. The solvent was removed from the filtrate in vacuo and the residue purified by flash chromatography by the method described above, giving a third crop (9.68 g) of product. Combined yield of product 57.27 g.

The combined product from the previous reaction (57.27 g), palladium on carbon (10%; 2.75 g), cyclohexene (81.4 ml) and ethyl acetate (2 L) were heated and stirred together under reflux under nitrogen for 24 hours. The solvent was evaporated and the residue dissolved in ethyl acetate (1 L) then filtered through a pad of Celite. The solvent was removed in vacuo to give an orange oil, which was dissolved in a mixture of ethanol (500 ml), water (500 ml) and triethylamine (55.2 ml). This mixture was stirred and heated under reflux for 3 hours. After cooling the ethanol was removed in vacuo and the remaining aqueous mixture extracted with ethyl acetate (2×250 ml). The combined extracts were washed with hydrochloric acid (1 M; 2×250 ml) then water then dried over magnesium sulphate. The solvent was removed in vacuo and the residue purified by flash chromatography over silica eluting with a 3:1, followed by a 1:1, mixture of petroleum ether (b.p. 40–60° C.) and ethyl acetate. Appropriate fractions were combined and the solvent removed in vacuo to give (S)-2-hydroxymethyl-1,4-benzodioxan-8-carboxaldehyde (8.02 g).

A mixture of the product from the previous reaction (2.0 g), potassium hydroxide (0.16 g), hydrazine hydrate (1.0 ml) and ethane-1,2-diol (50 ml) was stirred and heated under reflux for 1 hour. Excess hydrazine hydrate was distilled off until the internal temperature reached 185° C., then the remaining mixture was heated under reflux for a further 2 hours, cooled, and poured into water. The mixture was extracted with ethyl acetate (100 ml) and the combined extracts washed with dilute hydrochloric acid (100 ml), then saturated aqueous sodium hydrogen carbonate solution (100 ml) and dried over magnesium sulphate. The solvent was removed in vacuo and the residue purified by chromatography over silica eluting with a 20:1 mixture of dichloromethane and methanol giving (S)-8-methyl-1,4-benzodioxan-2-ylmethanol (0.9 g).

A solution of 4-toluenesulphonyl chloride (0.96 g) in dry pyridine (10 ml) was added to an ice-cold solution of the product from the previous reaction (0.9 g) in dry pyridine (40 ml) and the mixture stirred and allowed to warm to ambient temperature during 18 hours, then poured onto ice. The mixture was acidified with dilute hydrochloric acid then extracted with ether (2×200 ml). The combined extracts were washed with water and dried over magnesium sulphate. The solvent was evaporated and the residue purified by chromatography over silica eluting with a 4:1 mixture of petroleum ether (b.p. 40–60° C.) and ether. Appropriate fractions were combined and the solvent evaporated to give (R)-8-methyl-1,4-benzodioxan-2-ylmethyl 4-toluenesulphonate (0.91 g).

Trifluoroacetic acid (5 ml) was added to a solution of N-[(1-tert-butoxycarbonyl-4-piperidyl)methyl]pyridine-2-carboxamide (0.9 g) in dichloromethane (30 ml) and the mixture stirred at ambient temperature for 2 hours. The solvents were removed in vacuo and the residue dissolved in dry acetonitrile (20 ml). The product from the previous reaction (0.85 g) and potassium carbonate (2.0 g) were added to this solution and the mixture stirred and heated under reflux for 24 hours. The cooled solution was filtered and the filtrate partitioned between dichloromethane (100 ml) and water (100 ml). The organic layer was washed with water then dried over magnesium sulphate and the solvent removed in vacuo. The residue was purified by flash chromatography over silica eluting with a 9:1 mixture of dichloromethane and methanol. Appropriate fractions were combined and the solvent evaporated to give (S)-2-amino-N-{[1-(8-methyl-1,4-benzodioxan-2-ylmethyl)-4-piperidyl]methyl}pyridine-3-carboxamide (0.42 g) m.p. 56–58° C. $[\alpha]_D$ (c=0.869, methanol).

EXAMPLE 14

A mixture of 6-methylpyridine-2,3-dicarboxylic acid (19.75 g) and acetic anhydride (51 ml) was stirred and heated in an oil bath (bath temperature 110° C.) for 5 hours. The solvent was removed in vacuo and a 2:1 mixture of dichloromethane and ether was added, giving a dark brown solid. A solution of this solid in dichloromethane was passed through a pad of silica gel, eluting with dichloromethane, and the solvent was then evaporated to give partially purified 6-methylpyridine-2,3-dicarboxylic acid anhydride (12.1 g).

Trimethylsilyl azide (1.63 ml) was added to a solution of the product of the previous reaction (2.0 g) in ethanol free chloroform (10 ml) under nitrogen, giving a milky suspension which cleared on warming for 10 minutes. After one hour at ambient temperature the mixture was heated at 95–100° C. for one hour, cooled, and ethanol (0.72 ml) was added. The mixture was cooled in ice and the precipitated yellow solid collected to give 7-methylpyrido[2,3-d][1,3]oxazine-2,4-(1H)-dione (1.2 g).

A mixture of the product from the previous reaction (0.35 g) and [1-(7-chloro-1,4-benzodioxan-2-ylmethyl)4-piperidyl]methylamine (0.58 g) in 1,2-dimethoxyethane (15 ml) was stirred at ambient temperature for 24 hours. The solvent was removed in vacuo and the residue purified by flash chromatography on silica eluting with a 95:5 mixture of dichloromethane and methanol. Appropriate fractions were combined and the solvent removed in vacuo to give (S)-2-amino-N-{[1-(7-chloro-1,4-benzodioxan-2-ylmethyl)-4-piperidyl]methyl}-6-methylpyridine-3-carboxamide (0.3 g) m.p. 160–163° C. $[\alpha]_D$ −50.7° (c=0.036, methanol).

EXAMPLE 15

Trifluoroacetic acid (8 ml) was added to a solution of N-[(1-tert-butoxycarbonyl-4-piperidyl)methyl]pyridine-2-carboxamide (1.0 g) in dichloromethane (50 ml) and the mixture stirred at ambient temperature for 1 hour. The solvents were removed in vacuo and the residue dissolved in dry acetonitrile (50 ml). Potassium carbonate (1.5 g) and (R)-1,4-benzodioxan-2-ylmethyl 4-toulenesulphonate (0.89 g) were added and the mixture stirred and heated under reflux for 4 hours. The solvent was removed in vacuo and the residue partitioned between water (40 ml) and dichloromethane (40 ml). The organic phase was extracted with hydrochloric acid (2M, 40 ml) then the extracts basified with aqueous sodium hydroxide solution (5 M) and extracted with dichloromethane (3×20 ml). The combined organic extracts were dried over magnesium sulphate and the solvent removed in vacuo. The residue was purified by flash chromatography over silica eluting with a 9:1 mixture of dichloromethane and industrial methylated spirit. Appropriate fractions were combined and the solvent removed in vacuo to leave an oil which was treated with an ethereal solution of maleic acid. The resultant salt was collected but found to be very hygroscopic and was therefore taken up in aqueous sodium hydroxide solution (2 M) and the mixture extracted with dichloromethane. The extracts were dried over magnesium sulphate and the solvent removed in vacuo to give (S)-2-amino-N-{[1-(1,4-benzodioxan-2-ylmethyl)-4-piperidyl]methyl}pyridine-3-carboxamide as a colourless foam (0.18 g) m.p. 102–105° C. $[\alpha]_D$ −29.36° (c=0.6845, methanol).

EXAMPLE 16

A solution of 2H-thieno[3,2-d][1,3]oxazine-2,4(1H)-dione (3.1 g) and 4-(aminomethyl)-1-tert-butoxycarbonylpiperidine (3.9 g) in 1,2-dimethoxyethane (50 ml) was stirred at ambient temperature for 5 hours. The solvent was removed in vacuo and the residue purified by flash chromatography over silica eluting with ether. Appropriate fractions were combined and the solvent evaporated to give 3-amino-N-(1-tert-butoxycarbonyl-4-piperidylmethyl) thiophene-2-carboxamide as a colourless solid (2.57 g).

Trifluoroacetic acid (10 ml) was added to a suspension of the product from the previous reaction (2.0 g) in dichloromethane and the mixture stirred at ambient temperature for 18 hours. The solvents were removed in vacuo and the residue dissolved in acetonitrile (100 ml). To this solution was added potassium carbonate (3.1 g), triethylamine (2 ml) and 1,4-benzodioxan-2-ylmethyl 4-toluenesulphonate (1.8 g). The mixture was stirred and heated under reflux for 6 hours, more triethylamine (4 ml) was added and reflux continued for a further 6 hours. The cooled mixture was filtered and the solvent removed in vacuo. The residue was dissolved in dichloromethane, washed with water (2×50 ml), dried over magnesium sulphate, and the solvent removed in vacuo. The residue was purified by flash chromatography over silica eluting with dichloromethane followed by a 19:1 mixture of dichloromethane and industrial methylated spirit. Appropriate fractions were combined and the solvent removed in vacuo to give an oil which on trituration with ether gave 3-amino-N-{[1-(1,4-benzodioxan-2-ylmethyl)-4-piperidyl]methyl}thiophene-2-carboxamide as a solid (0.22 g) m.p. 144–146° C.

EXAMPLE 17

Trifluoroacetic acid (5 ml) was added to a suspension 3-amino-N-(1-tert-butoxycarbonyl-4-piperidylmethyl) thiophene-2-carboxamide (3.8 g) in dichloromethane (100 ml) and the mixture stirred at ambient temperature for 18 hours. The solvents were removed in vacuo and the residue dissolved in acetonitrile (100 ml). To this solution was added potassium carbonate (1.4 g), triethylamine (4 ml) and (R)-7-chloro-1,4-benzodioxan-2-ylmethyl 4-toluenesulphonate (3.5 g) and the mixture stirred and heated under reflux for 3 days. The mixture was cooled and filtered and the solvent removed in vacuo to give an oil, which was dissolved in dichloromethane (100 ml) and washed with water (2×50 ml). The solution was dried over magnesium sulphate and the solvent removed in vacuo. The residue was purified by flash chromatography over silica eluting with dichloromethane, then a 19:1 mixture of dichloromethane and industrial methylated spirit. Appropriate fractions were combined and the solvent removed in vacuo to give a pale yellow solid which was triturated with ether to give (S)-3-amino-N-{[1-(7-chloro-1,4-benzodioxan-2-ylmethyl)-4-piperidyl] methyl}thiophene-2-carboxamide as a pale yellow solid (100 mg) m.p. 200–202° C. $[\alpha]_D$ −30° (c=0.224, ethanol).

EXAMPLE 18

Triethylamine (0.47 ml) was added to a suspension of 2-methylpyridine-3-carboxylic acid (0.46 g) in dichloromethane and the mixture cooled in ice water. Ethyl chloroformate (0.33 ml) was added with stirring and the mixture allowed to warm to ambient temperature during 18 hours. (S)-4-(Aminomethyl)-1-(7-chloro-1,4-benzodioxan-2-ylmethyl)piperidine (1.0 g) was added and stirring continued for 24 hours. The solvent was evaporated and the residue triturated with water, collected by filtration, and purified by flash chromatography over silica eluting with a 3:1, then a 2:1, then a 1:1 mixture of ethyl acetate and methanol. Appropriate fractions were combined and the solvent removed in vacuo to give still impure product. Repeat flash chromatography over silica eluting with a 10:1 mixture of dichloromethane and methanol, then an 18:1:1 mixture of dichloromethane, methanol and triethylamine, followed by removal of solvent in vacuo from the appropriate fractions, gave (S)-N-{[1-(7-chloro-1,4-benzodioxan-2-ylmethyl)-4-piperidyl]methyl}-2-methylpyridine-3-carboxamide (330 mg) as a colourless solid m.p. 133–136° C. $[\alpha]_D$ −46.6° (c=0.837, methanol).

EXAMPLE 19

A solution of 2-chloropyridine-3-carboxylic acid (4.09 g) and 1-methylmorpholine (2.7 ml) in dichloromethane (100 ml) was stirred at −5° C. under nitrogen and ethyl chloroformate (2.4 ml) was added dropwise. After 10 minutes a solution of N-benzylidene-1-(4-piperidyl)methylamine (5.0 g) in dichloromethane (25 ml) was added and stirring continued at −5° C. for 2 hours then at ambient temperature for 18 hours. The solvent was removed in vacuo and the residue stirred with potassium hydrogen sulphate solution (1 M; 250 ml) for 5 hours. The mixture was filtered and the filtrate washed with dichloromethane (2×150 ml), basified with aqueous sodium hydroxide solution (5 M) and extracted with dichloromethane (3×150 ml). The combined extracts were dried over magnesium sulphate and the solvent was evaporated to give 4-(aminomethyl)-1-(2-chloro-3-pyridylcarbonyl)-piperidine (4.81 g) contaminated with some 1-methylmorpholine. This material was used in the next reaction without further purification.

A mixture of the crude product from the previous reaction (4.75 g), potassium carbonate (12.93 g) and (R)-7-chloro-1,4-benzodioxan-2-ylmethyl 4-toluenesulphonate (6.64 g) in dry acetonitrile (100 ml) was stirred and heated under reflux for 48 hours. The mixture was cooled and filtered and the solvent removed in vacuo to give an oil which was purified by flash chromatography over silica eluting with a 25:1 mixture of dichloromethane and industrial methylated spirit. Appropriate fractions were combined and the solvent removed in vacuo to give (S)-4-[N-(7-chloro-1,4-benzodioxan-2-ylmethyl)aminomethyl]-1-(2-chloronicotinoyl)piperidine ethanol solvate (2.49 g) as a gum.

A mixture of the product from the previous reaction (2.49 g), industrial methylated spirit (10 ml), aqueous ammonia solution (S.G. 0.88; 100 ml) and copper lining powder (0.5 g) was stirred and heated in a pressure vessel at 150° C. for 18 hours. After cooling dichloromethane (400 ml) and water (400 ml) were added and the mixture filtered through Celite, washing through with water (4×50 ml) followed by dichloromethane (4×50 ml). The filtrate layers were separated and the aqueous extracted with dichloromethane (400 ml). The combined organics were dried over magnesium sulphate then the solvent was evaporated to leave a red oil which was purified by flash chromatography over silica eluting with a 9:1 mixture of dichloromethane and ethanol. Appropriate fractions were combined and the solvent removed in vacuo to give the product as a red gum, which was dissolved in hot ethanol (20 ml) and a hot solution of fumaric acid (340 mg) in ethanol (5 ml) was added. The solvent was removed in vacuo and the residue triturated with ether to give racemic 1-(2-aminonicotinoyl)-4-[N-(7-chloro-1,4-benzodioxan-2-ylmethyl)aminomethyl]piperidine 1.6 fumarate 0.7 hydrate 0.7 ethanol solvate (0.85 g) m.p. 110° C. (dec.) $[\alpha]_D$ 0°.

EXAMPLE 20

A mixture of 2-fluoro-6-trifluoromethylbenzaldehyde (25 g) and aqueous sodium hydroxide solution (0.5 M; 866 ml) was stirred and heated at 80° C. under nitrogen for 43 hours. The cooled solution was washed with ether (2×350 ml), acidified with concentrated hydrochloric acid, then extracted with ether (2×500 ml). The combined extracts were dried over magnesium sulphate and the solvent removed in vacuo. The residue was purified by flash chromatography over silica eluting with a 95:5 mixture of dichloromethane and methanol. Appropriate fractions were combined and the solvent removed in vacuo to give 2-hydroxy-6-trifluoromethylbenzaldehyde (6.2 g) as an oil.

A mixture of the product from the previous reaction (5.95 g), (R)-glycidyl 4-toluenesulphonate (6.05 g) and potassium carbonate (4.3 g) in dimethylformamide (150 ml) was stirred and heated at 60° C. for 24 hours. The cooled solution was poured into ice water (600 ml) and extracted with ether (3×300 ml). The combined extracts were washed with brine (2×400 ml), dried over magnesium sulphate and the solvent removed in vacuo to give a solid (7.0 g), which was recrystallised from ether (30 ml) to give (R)-2-(2,3-epoxypropoxy)-6-trifluoromethylbenzaldehyde as a solid (5.4 g).

A mixture of the product from the previous reaction (5.4 g) and 3-chloroperoxybenzoic acid (57%, 13.84 g) in chloroform (300 ml) was stirred and heated under reflux for 18 hours, then allowed to stand at ambient temperature for 3 days before pouring into saturated aqueous sodium hydrogen carbonate solution (400 ml). The mixture was extracted with dichloromethane (200 ml), the organic phase washed with saturated aqueous sodium bicarbonate solution (3×400 ml) then dried over magnesium sulphate and the solvent removed in vacuo to give crude 2-(2,3-epoxypropoxy)-6-trifluoromethylphenyl formate (6.26 g) as a yellow solid.

A solution of the crude product from the previous reaction (6.26 g) in methanol (75 ml) was added dropwise to a solution of sodium methoxide prepared by dissolution of sodium metal (0.69 g) in methanol (75 ml) and the mixture stirred at ambient temperature for 18 hours, then allowed to stand for 24 hours. The solvent was removed in vacuo and the residue added to water (300 ml). The mixture was extracted with ethyl acetate (3×200 ml), the combined extracts dried over magnesium sulphate, and the solvent removed in vacuo to give a brown oil which was purified by flash chromatography over silica eluting with a 1:1 mixture of petroleum ether (b.p. 40–60° C.) and ethyl acetate. Appropriate fractions were combined and the solvent removed in vacuo to give (S)-8-trifluoromethyl-1,4-benzodioxan-2-ylmethanol (1.80 g) as a yellow oil.

4-Toluenesulphonyl chloride (1.29 g) was added to a solution of the product from the previous reaction (1.26 g) in dry pyridine (50 ml) at −10° C. under nitrogen and the mixture allowed to warm to ambient temperature while stirring for 18 hours. More 4-toluenesulphonyl chloride (0.7 g) was added and stirring continued for 3 days, then the mixture was poured into dilute hydrochloric acid (200 ml) and extracted with ethyl acetate (2×300 ml). The combined extracts were washed with dilute hydrochloric acid (2×200 ml), dried over magnesium sulphate, and the solvent removed in vacuo to give crude (R)-8-trifluoromethyl-1,4-benzodioxan-2-ylmethyl 4-toluenesulphonate (1.27 g).

Trifluoroacetic acid (15 ml) was added to a solution of 2-amino-N-[(1-tert-butoxycarbonyl-4-piperidyl)methyl]pyridine-3-carboxamide (1.5 g; prepared in a similar manner to that described in Example 2) in dichloromethane (15 ml) then the mixture stirred at ambient temperature for 3 hours and the solvent removed in vacuo. The residue was dissolved in acetonitrile (100 ml), potassium carbonate (4.5 g) and the product from the previous reaction (1.27 g) were added, and the mixture stirred and heated under reflux for 72 hours. The cooled solution was filtered, washing the solid with ethyl acetate (200 ml). The filtrate was evaporated in vacuo and the residue purified by flash chromatography over silica eluting with a 3:1 mixture of ethyl acetate and methanol. Appropriate fractions were combined and the solvent removed in vacuo to give (S)-2-amino-N-{[1-(8-trifluoromethyl-1,4-benzodioxan-2-ylmethyl)-4-piperidyl]methyl}pyridine-3-carboxamide (870 mg) as a colourless solid m.p. 101–103° C. $[\alpha]_D$ −16.2° (c=0.56, dichloromethane).

EXAMPLE 21

A mixture of 5-bromo-2-hydroxybenzaldehyde (68.75 g), (R)-glycidyl 4-toluenesulphonate (65 g) and potassium carbonate (47.3 g) in dry dimethylformamide (1.5 L) was stirred and heated at 60° C. under nitrogen for 24 hours, then cooled and allowed to stand at ambient temperature for 24 hours. The mixture was poured into water (2 L) then extracted with ether (4×400 ml). The combined extracts were washed with brine (4×500 ml), dried over magnesium sulphate, and the solvent removed in vacuo to give an oil which was purified by flash chromatography over silica eluting with a 4:1 mixture of petroleum ether (b.p. 60–80° C.) and ethyl acetate. Appropriate fractions were combined and the solvent removed in vacuo to give an oil, which on trituration with ether (150 ml) gave (R)-5-bromo-2-(2,3-epoxypropoxy)benzaldehyde as a colourless solid (43.3 g).

A solution of the product from the previous reaction (42.6 g) and 3-chloroperoxybenzoic acid (86 %; 69.4 g) in chloroform (1.5 L) was heated under reflux for 24 hours then allowed to stand at ambient temperature for 48 hours. The solution was washed with water (5×300 ml), saturated aqueous sodium bicarbonate solution (600 ml) and brine (2×500 ml), then dried over magnesium sulphate. The solvent was removed in vacuo to give crude (R)-5-bromo-2-(2,3-epoxypropoxy)phenyl formate (47.8 g) as a yellow oil which crystallised on standing.

A solution of the crude product from the previous reaction (47.8 g) in methanol (400 ml) was added dropwise to a solution of sodium methoxide, prepared by dissolving sodium metal (5.3 g) in methanol (400 ml), and the mixture stirred at ambient temperature for 18 hours. The solvent was removed in vacuo, water (800 ml) was added to the residue and the mixture extracted with ethyl acetate (4×500 ml). The combined extracts were dried over magnesium sulphate and the solvent removed in vacuo to give a brown oil, which was purified by flash chromatography over silica eluting with a 5:1 mixture of petroleum ether (b.p. 60–80° C.) and ethyl acetate. Appropriate fractions were combined and the solvent removed in vacuo to give (S)-7-bromo-1,4-benzodioxan-2-ylmethanol (29.2 g) as an orange oil.

4-Toluenesulphonyl chloride (7.63 g) was added to an ice cooled solution of the product from the previous reaction (7.0 g) in pyridine (50 ml) and the mixture stirred at ambient temperature for 20 hours, then poured into hydrochloric acid (1 M; 200 ml). The mixture was extracted with ethyl acetate (3×200 ml) and the combined extracts washed with hydrochloric acid (1 M; 200 ml) then dried over magnesium sulphate. The solvent was removed in vacuo and the residue recrystallised from a 3:1 mixture of ether and ethyl acetate to give (R)-7-bromo-1,4-benzodioxan-2-ylmethyl 4-toluenesulphonate (6.9 g) as a colourless solid.

Trifluoroacetic acid (17 ml) was added to a solution of 2-amino-N-[(1-tert-butoxycarbonyl-4-piperidyl)methyl] pyridine-3-carboxamide (2.5 g; prepared in a similar manner to that described in Example 2) in dichloromethane (17 ml) then the mixture stirred at ambient temperature for 2 hours and the solvent removed in vacuo. The residue was dissolved in acetonitrile (170 ml) then potassium carbonate (7.6 g) and the product from the previous reaction (2.21 g) were added and the mixture heated under reflux for 24 hours then allowed to stand at ambient temperature for 36 hours before pouring into aqueous sodium hydroxide solution (5 M; 300 ml). The mixture was extracted with ethyl acetate (100 ml) and the organic phase washed with hydrochloric acid (1 M; 2×300 ml). The combined acid extracts were basified with aqueous sodium hydroxide solution (5 M; 200 ml) and the mixture extracted with ethyl acetate (3×200 ml). These combined extracts were dried over magnesium sulphate and the solvent removed in vacuo to give a colurless solid (1.3 g) which was recrystallised from a 5:1 mixture of ethyl acetate and petroleum ether (b.p. 40–60° C.) (7 ml) giving (S)-2-amino-N-{[1-(7-bromo-1,4-benzodioxan-2-ylmethyl)-4-piperidyl]methyl}pyridine-3-carboxamide (0.82 g) m.p. 158–160° C. $[\alpha]_D$ −25.5° (c=79, dichloromethane).

EXAMPLE 22

A solution of 3-pyridinecarbonyl chloride hydrochloride (3.87 g) in dichloromethane (100 ml) was added to a suspension of 4-(aminomethyl)-1-tert-butoxycarbonylpiperidine (5.0 g) and potassium carbonate (10 g) in dichloromethane (100 ml), and the mixture stirred at ambient temperature for 2 hours before pouring into water (500 ml). The organic layer was washed with water (250 ml), dried over magnesium sulphate and the solvent was evaporated. The residue was purified by flash chromatography over silica eluting with a 20:1 mixture of dichloromethane and methanol. Appropriate fractions were combined and the solvent removed in vacuo to give N-[(1-tert-butoxycarbonyl-4-piperidyl)methyl]pyridine-3-carboxamide (3.22 g) as an orange oil.

Trifluoroacetic acid (10 ml) was added to a solution of the product from the previous reaction (0.95 g) in dichloromethane (25 ml) and the mixture stirred for 2 hours, then the solvent was removed in vacuo. The residue was dissolved in dry acetonitrile (25 ml), potassium carbonate (5.0 g) and (R)-7-chloro-1,4-benzodioxan-2-ylmethyl 4-toluenesulphonate (1.0 g) were added and the mixture stirred and heated under reflux for 24 hours. The cooled mixture was filtered, the filtrate evaporated in vacuo. The residue was purified by flash chromatography over silica eluting with a 20:1 mixture of dichloromethane and methanol. Appropriate fractions were combined and the solvent removed in vacuo to give (S)-N-{[1-(7-chloro-1,4-benzodioxan-2-ylmethyl)-4-piperidyl]methyl}pyridine-3-carboxamide (0.75 g) m.p. 172–4° C. $[\alpha]_D$ −48° (c=0.9945, methanol).

EXAMPLE 23

Trifluoroacetic acid (10 ml) was added to a solution of N-[(1-tert-butoxycarbonyl-4-piperidyl)methyl]quinoline-8-carboxamide (1.51 g; prepared in a similar manner to that described in Example 8) in dichloromethane (50 ml), the mixture stirred for 2 hours, then the solvent was removed in vacuo. The residue was dissolved in dry acetonitrile (30 ml), potassium carbonate (3.0 g) and (R)-7-chloro-1,4-benzodioxan-2-ylmethyl 4-toluenesulphonate (1.51 g) were added and the mixture stirred and heated under reflux for 24 hours. The mixture was filtered and the solvent removed in vacuo. The residue was dissolved in dichloromethane and the solution washed with water (2×50 ml) then dried over magnesium sulphate. The solvent was evaporated and the residue purified by flash chromatography over silica eluting with dichloromethane then a 100:1 followed by a 20:1 mixture of dichloromethane and methanol. Appropriate fractions were combined and the solvent removed in vacuo to give (S)-N-{[1-(7-chloro-1,4-benzodioxan-2-ylmethyl)-4-piperidyl]methyl}quinoline-8-carboxamide (1.33 g) m.p. 51–54° C. $[\alpha]_D$ −39.7° (c=0.7230, methanol).

EXAMPLE 24

Trifluoroacetic acid (10 ml) was added to a solution of N-[(1-tert-butoxycarbonyl-4-piperidyl)methyl]pyridine-3-carboxamide (1.56 g) in dichloromethane (25 ml) and the mixture stirred for 2 hours then the solvent was removed in vacuo. The residue was dissolved in dry acetonitrile (10 ml) and potassium carbonate (5.0 g) was added, followed by a solution of (R)-7-chloro-1,4-benzodioxan-2-ylmethyl 4-toluenesulphonate (1.7 g) in dry acetonitrile (15 ml), and the mixture was stirred and heated under reflux for 6 hours. The cooled mixture was poured into water then extracted with dichloromethane (2×100 ml). The combined extracts were washed with brine (100 ml), dried over magnesium sulphate, and the solvent removed in vacuo. The residue was purified by flash chromatography over silica eluting with a 20:1 mixture of dichloromethane and methanol. Appropriate fractions were combined and the solvent removed in vacuo to give (S)-N-{[1-(8-chloro-1,4-benzodioxan-2-ylmethyl)-4-piperidyl]methyl}pyridine-3-carboxamide (1.04 g) as a colourless solid m.p. 52–54° C. $[\alpha]_D$ −35.3° (c=1.024, methanol).

EXAMPLE 25

A mixture of (S)-4-(aminomethyl)-1-(7-chloro-1,4-benzodioxan-2-ylmethyl)-piperidine (0.57 g) and 6-methylpyridine-2-carboxylic acid (0.27 g) in xylene (50 ml) was heated under a Dean and Stark water separator for 6 hours. The solvent was removed in vacuo from the cooled mixture and the residue was dissolved in dichloromethane (100 ml). This solution was washed with water (2×100 ml), dried over magnesium sulphate and the solvent was evaporated. The residue was purified by flash chromatography over silica eluting with a 20:1 mixture of dichloromethane and methanol. Appropriate fractions were combined and the solvent removed in vacuo to give an oil (0.15 g), which was dissolved in methanol (10 ml) then fumaric acid (0.04 g) was added. The solvent was removed in vacuo to give (S)-N-{[1-(7-chloro-1,4-benzodioxan-2-ylmethyl)-4-piperidyl] methyl}-6-methylpyridine-2-carboxamide difumarate (0.19 g) as a beige solid m.p. 81–3° C. $[\alpha]_D$ −39.6° (c=0.389, methanol).

EXAMPLE 26

2-Methoxypyridine-3-carboxylic acid (4.86 g) was added in portions to thionyl chloride (50 ml) then the mixture stirred and heated under reflux for 2 hours. After cooling, excess thionyl chloride was removed in vacuo and the residue dissolved in dichloromethane (100 ml). A solution of 4-(aminomethyl)-1-tert-butoxycarbonylpiperidine (7.3 g) in dichloromethane (100 ml) was added and the mixture stirred at ambient temperature for 4 hours then poured into water (200 ml). The organic phase was washed with water (100 ml), aqueous oxalic acid solution (2 M; 2×100 ml), hydrochloric acid (1 M; 100 ml), aqueous sodium hydrogen carbonate solution (2 M; 2×150 ml), then water, and dried over magnesium sulphate. The solvent was removed in vacuo and the residue purified by flash chromatography over silica eluting with a 1:1 mixture of ethyl acetate and petroleum ether (b.p. 60–80° C.). Appropriate fractions were combined and the solvent removed in vacuo to give N-[(1-tert-butoxycarbonyl-4-piperidyl)methyl]-2-methoxypyridine-3-carboxamide (2.06 g)

Trifluoroacetic acid (10 ml) was added to a solution of the product from the previous reaction (2.06 g) in dichloromethane (25 ml) and the mixture stirred for 2½ hours, then the solvent was removed in vacuo. The residue was dissolved in dry acetonitrile (50 ml) and potassium carbonate (12 g) was added followed by a solution of (R)-7-chloro-1,4-benzodioxan-2-ylmethyl 4-toluenesulphonate (2.33 g) in dry acetonitrile (15 ml) and the mixture was stirred and heated. under reflux for 24 hours. The cooled mixture was filtered and the solvent removed in vacuo. The residue was dissolved in dichloromethane (200 ml), and the solution washed with water (2×200 ml) and dried over magnesium sulphate. The solvent was removed in vacuo and the residue purified by flash chromatography over silica eluting with a 20:1 mixture of dichloromethane and methanol. Appropriate fractions were combined and the solvent removed in vacuo to give (S)-N-{[1-(7-chloro-1,4-benzodioxan-2-ylmethyl)-4-piperidyl]methyl}-2-methoxypyridine-3-carboxamide 0.6 hydrochloride 0.9 hydrate (1.21 g) as a solid m.p. 72–75° C. $[\alpha]_D$ −47.3° (c=0.226, methanol).

EXAMPLE 27

The solvent was evaporated in vacuo at ambient temperature from a solution of butyllithium in hexanes (2.5 M; 55.6 ml) giving a viscous oil, which was cooled to −78° C. under nitrogen and a pre-cooled solution of potassium tert-butoxide (15.6 g) in tetrahydrofuran (280 ml) was added slowly. 3,4-Difluoroanisole (20.0 g) was then added dropwise, maintaining the reaction temperature below −60° C., giving a brown solution. After stirring for 2 hours at −78° C., dry dimethylformamide (10.8 ml) was added and the mixture allowed to warm to ambient temperature over 18 hours. Water (200ml) was added and the mixture extracted with ether (3×300 ml). The combined extracts were washed with aqueous lithium chloride solution (40%; 100 ml), water (200 ml) and dried over magnesium sulphate. The solvent was evaporated to give an orange oil (23.0 g) which was purified by flash chromatography over silica eluting with a 9:1 mixture of petroleum ether (b.p. 40–60° C.) and ethyl acetate. Appropriate fractions were combined and the solvent removed in vacuo to give 2,3-difluoro-6-methoxybenzaldehyde (10.1 g) as a yellow solid.

A solution of boron tribromide in dichloromethane (1.0 M; 197.4 ml) was added to a solution of 2,3-difluoro-6-methoxybenzaldehyde (10.4 g; prepared in a similar manner to that described above) in dichloromethane (100 ml) under nitrogen stirring below −20° C. The resulting solution was allowed to warm to ambient temperature overnight, then methanol (200 ml) followed by water (100 ml) were added, and the mixture heated at 40° C. for 2 hours. The aqueous layer was separated and extracted with dichloromethane (2×300 ml). The combined organic solutions were extracted with aqueous sodium hydroxide solution (1 M; 3×400 ml) and the combined extracts acidified with concentrated hydrochloric acid, then extracted with ethyl acetate (3×300 ml). These combined extracts were dried over magnesium sulphate and the solvent removed in vacuo to give 2,3-difluoro-6-hydroxybenzaldehyde (8.12 g) as a solid.

A mixture of the product from the previous reaction (8.1 g), (R)-glycidyl 4-toluenesulphonate (11.4 g) and potassium carbonate (7.03 g) in dimethylformamide (250 ml) was stirred and heated at 60° C. under nitrogen for 3 days. Water (300 ml) was added and the mixture extracted with ether (3×400 ml). The combined extracts were washed with aqueous lithium chloride solution (40%; 200 ml), water (200 ml) and dried over magnesium sulphate.The solvent was evaporated to give an oil, to which was added a 1:1 mixture of ether and petroleum ether (b.p. 40–60° C.) giving an orange solution which was decanted from a dark brown oil. The solvent was removed in vacuo from the orange solution to give (R)-6-(2,3-epoxypropoxy)-2,3-difluorobenzaldehyde (9.0 g) as an oil.

A solution of the product from the previous reaction (9.0 g) and 3-chloroperoxybenzoic acid (57%; 26.47 g) in chloroform (500 ml) was heated under reflux for 18 hours. Saturated aqueous sodium hydrogen carbonate solution (300 ml) and dichloromethane (500 ml) were added, then the organic layer separated and washed with saturated aqueous sodium hydrogen carbonate solution (3×300 ml), brine (300 ml) and dried over magnesium sulphate. The solvent was removed in vacuo to give crude (R)-6-(2,3-epoxypropoxy)-2,3-difluorophenyl formate (11.9 g) as a solid.

A solution of the crude product from the previous reaction (11.9 g) in methanol (140 ml) was added dropwise under nitrogen to a stirred solution of sodium methoxide, prepared by dissolving sodium metal (1.22 g) in methanol (140 ml), and the solution allowed to stand at ambient temperature for 18 hours. The solvent was removed in vacuo, water (500 ml) was added to the residue, then the mixture extracted with ethyl acetate (3×400 ml). The combined extracts were washed with brine (300 ml), dried over magnesium sulphate, and the solvent removed in vacuo. The residue was purified by flash chromatography over silica eluting with a 1:1 mixture of ethyl acetate and petroleum ether (b.p. 40–60° C.). Appropriate fractions were combined and the solvent removed in vacuo to give (S)-7,8-difluoro-1,4-benzodioxan-2-ylmethanol (0.7 g) as an oil.

A solution of 4-toluenesulphonyl chloride (0.74 g) in dichloromethane (10 ml) was added dropwise to a solution of the product from the previous reaction (0.7 g) and 4-(dimethylamino)pyridine (0.52 g) in dichloromethane (10 ml) at 0° C. under nitrogen. The solution was stirred for 2 hours at 0° C., then at ambient temperature for 1 hour. Water (50 ml) was added and the mixture extracted with dichloromethane (3×100 ml). The combined extracts were dried over magnesium sulphate and the solvent was evaporated to give (R)-7,8-difluoro-1,4-benzodioxan-2-ylmethyl 4-toluenesulphonate (1.1 g) a yellow oil which crystallised on standing.

Trifluoroacetic acid (10 ml) was added to a solution of 2-amino-N-[(1-tert-butoxycarbonyl-4-piperidyl)methyl] pyridine-3-carboxamide (1.48 g, prepared in a similar manner to that described in Example 2) in dichloromethane (10 ml) then the mixture stirred at ambient temperature for 5 hours and the solvent removed in vacuo. The residue was added to a mixture of potassium carbonate (4.3 g), potassium iodide (10 mg) and the product from the previous reaction (1.1 g) in acetonitrile (100 ml), and the mixture stirred and heated under reflux for 16 hours. The solvent was removed in vacuo from the cooled mixture and the residue partitioned between saturated aqueous sodium hydrogen carbonate solution (300 ml) and ethyl acetate (300 ml). The aqueous layer was further extracted with ethyl acetate (3×300 ml) and the combined organics washed with brine (400 ml) and dried over magnesium sulphate. The solvent was removed in vacuo and the residue purified by flash chromatography over silica eluting with a 9:1 mixture of ethyl acetate and methanol. Appropriate fractions were combined and the solvent removed in vacuo to give (S)-2-amino-N-{[1-(7,8-difluoro-1,4-benzodioxan-2-ylmethyl)4-piperidyl]methyl}pyridine-3-carboxamide 0.2 ethyl acetate solvate as a buff solid (0.47 g) m.p. 127–128° C. $[\alpha]_D$ –25.8° (c=0.80, dichloromethane).

EXAMPLE 28

A mixture of pyrogallol carbonate (8.2 g), (S)-epichlorohydrin (5.0 g) and dry pyridine (0.2 ml) in dry ethyl acetate (50 ml) was heated under reflux for 2 hours. The solvent was removed in vacuo, water (30 ml) was added, and the mixture heated under reflux for 30 minutes. A solution of potassium hydroxide (10 g) in water (20 ml) was added dropwise and the mixture heated under reflux under nitrogen for a further 30 minutes. The cooled mixture was diluted with water (100 ml), acidified with hydrochloric acid (5 M) then extracted with ethyl acetate (3×200 ml). The combined extracts were washed with water (2×100 ml) and dried over magnesium sulphate. The solvent was removed in vacuo and the residue purified by chromatography over silica eluting with a 1:1 mixture of ethyl acetate and petroleum ether (b.p. 60–80° C.) followed by neat ethyl acetate. Appropriate fractions were combined and the solvent removed in vacuo to give (S)-8-hydroxy-1,4-benzodioxan-2-ylmethanol (0.8 g).

Trifluoromethanesulphonic anhydride (2.48 g) was added dropwise under nitrogen to a stirred solution of the product from the previous reaction (0.8 g) and 4-(dimethylamino) pyridine (0.64 g) in dichloromethane (50 ml) at 0° C. The mixture was allowed to warm to ambient temperature while stirring continued for 18 hours, then was washed with water (100 ml) and dried over magnesium sulphate. The solvent was removed in vacuo and the residue purified by flash chromatography over silica eluting with dichloromethane. Appropriate fractions were combined and the solvent removed in vacuo to give (R)-8-(trifluoromethane-sulphonyloxy)-1,4-benzodioxan-2-ylmethyl trifluoromethanesulphonate (1.10 g).

Trifluoroacetic acid (5 ml) was added to a solution of 2-amino-N-[(1-tert-butoxycarbonyl-4-piperidyl)methyl] pyridine-3-carboxamide 0.9 g; prepared in a similar manner to that described in Example 2) in dichloromethane (25 ml), then the mixture stirred at ambient temperature for 2 hours and the solvent removed in vacuo. The residue was dissolved in dry acetonitrile (25 ml), potassium carbonate (5.0 g) was added, followed by a solution of the product from the previous reaction (1.03 g) in dry acetonitrile (10 ml). The mixture was stirred and heated under reflux for 1½ hours, cooled and filtered, and the solvent removed in vacuo. The residue was dissolved in dichloromethane (100 ml) and washed with water (2×100 ml) and dried over magnesium sulphate. The solvent was removed in vacuo and the residue purified by flash chromatography over silica eluting with a 20:1 mixture of ethyl acetate and methanol. Appropriate fractions were combined and the solvent removed in vacuo to give (S)-2-amino-N-{[1-(8-trifluoromethane-sulphonyloxy-1,4-benzodioxan-2-ylmethyl)-4-piperidyl] methyl}pyridine-3-carboxamide 0.17 g) as a colourless solid m.p. 52–55° C. $[\alpha]_D$ –21.9° (c=0.2925, methanol)

EXAMPLE 29

N,N'-Carbonyl diimidazole (6.58 g) was added to a suspension of pyridine-2-carboxylic acid (5.0 g) in dichloromethane (75 ml) stirring under nitrogen at ambient temperature. Stirring continued until gas evolution had ceased (~2 hours) then N-benzylidene-1-(4-piperidyl)methylamine (8.2 g) was added and the reaction mixture stirred for 18 hours. The solvent was evaporated to give a viscous yellow oil, which was then stirred with aqueous potassium hydrogen sulphate solution (1 M; 200 ml) for 18 hours. The mixture was washed with dichloromethane (2×250 ml) and adjusted to pH 14 with aqueous sodium hydroxide solution (5 M) then extracted with methane (3×250 ml). The combined extracts were dried over magnesium and the the solvent removed in vacuo to give 4-(aminomethyl)-1-(2-pyridylcarbonyl)piperidine (5.2 g) as a viscous yellow oil.

A mixture of the product of the previous reaction (3.0 g), (R)-7-chloro-1,4-benzodioxan-2-ylmethyl 4-toluenesulphonate (4.86 g), potassium iodide (200 mg) and potassium carbonate (9.45 g) in dry acetonitrile was stirred and heated under reflux for 18 hours. The mixture was cooled and filtered and the solvent removed in vacuo. The residue was purified by flash chromatography over silica eluting with a 20:1 mixture of dichloromethane and industrial methylated spirit. Appropriate fractions were combined and the solvent removed in vacuo giving a viscous yellow oil (2.87 g), which was dissolved in hot ethanol (10 ml) and treated with a solution of fumaric acid (0.76 g) in hot ethanol (10 ml). The solvent was removed in vacuo and the residue triturated with ether (250 ml) to give 4-[N-(7-chloro-1,4-benzodioxan-2-ylmethyl)aminomethyl]-1-(2-pyridylcarbonyl)piperidine 1.2 fumarate 0.5 hydrate 0.4 solvate as a solid m.p. ~55° C. (dec.) $[\alpha]_D$ –42.9° (c=0.8135, methanol).

EXAMPLES 30–52

The following compounds of formula I were made by the method detailed below:

| Example No. | Name |
|---|---|
| 30 | (S)-N-{[1-(7-methyl-1,4-benzodioxan-2-ylmethyl)-4-piperidyl]methyl}pyridine-3-carboxamide |
| 31 | (S)-2-methyl-N-{[1-(7-methyl-1,4-benzodioxan-2-ylmethyl)-4-piperidyl]-methyl}pyridine-3-carboxamide |
| 32 | (S)-N-{[1-(7-methyl-1,4-benzodioxan-2-ylmethyl)-4-piperidyl]methyl}-6-(1-pyrrolyl)pyridine-3-carboxamide |
| 33 | (S)-N-{[1-(7-methyl-1,4-benzodioxan-2-ylmethyl)-4-piperidyl]methyl}-2-(methylthio)pyridine-3-carboxamide |
| 34 | (S)-5-bromo-N-{[1-(7-methyl-1,4-benzodioxan-2-ylmethyl)-4-piperidyl]-methyl}pyridine-3-carboxamide |
| 35 | (S)-N-{[1-(7-bromo-1,4-benzodioxan-2-ylmethyl)-4-piperidyl]methyl}pyridine-3-carboxamide |
| 36 | (S)-N-{[1-(7-bromo-1,4-benzodioxan-2-ylmethyl)-4-piperidyl]methyl}-2-methylpyridine-3-carboxamide |
| 37 | (S)-N-{[1-(7-bromo-1,4-benzodioxan-2-ylmethyl)-4-piperidyl]methyl}-6-(1-pyrrolyl)pyridine-3-carboxamide |
| 38 | (S)-N-{[1-(7-bromo-1,4-benzodioxan-2-ylmethyl)-4-piperidyl]methyl}-2-(methylthio)pyridine-3-carboxamide |
| 39 | (S)-5-bromo-N-{[1-(7-bromo-1,4-benzodioxan-2-ylmethyl)-4-piperidyl]methyl}pyridine-3-carboxamide |
| 40 | (S)-N-{[1-(7-chloro-1,4-benzodioxan-2-ylmethyl)-4-piperidyl]methyl}-6-(1-pyrrolyl)pyridine-3-carboxamide |
| 41 | (S)-N-{[1-(7-chloro-1,4-benzodioxan-2-ylmethyl)-4-piperidyl]methyl}-2-(methylthio)pyridine-3-carboxamide |
| 42 | (S)-5-bromo-N-{[1-(7-chloro-1,4-benzodioxan-2-ylmethyl)-4-piperidyl]methyl}pyridine-3-carboxamide |
| 43 | (S)-N-{[1-(7-fluoro-1,4-benzodioxan-2-ylmethyl)-4-piperidyl]methyl}pyridine-3-carboxamide |
| 44 | (S)-N-{[1-(7-fluoro-1,4-benzodioxan-2-ylmethyl)-4-piperidyl]methyl}-2-(methylthio)pyridine-3-carboxamide |
| 45 | (S)-N-{[1-(8-trifluoromethyl-1,4-benzodioxan-2-ylmethyl)-4-piperidyl]methyl}pyridine-3-carboxamide |
| 46 | (S)-2-methyl-N-{[1-(8-trifluoromethyl-1,4-benzodioxan-2-ylmethyl)-4-piperidyl]methyl}pyridine-3-carboxamide |
| 47 | (S)-6-(1-pyrrolyl)-N-{[1-(8-trifluoromethyl-1,4-benzodioxan-2-ylmethyl)-4-piperidyl]methyl}pyridine-3-carboxamide |
| 48 | (S)-2-(methylthio)-N-{[1-(8-trifluoromethyl-1,4-benzodioxan-2-ylmethyl)-4-piperidyl]methyl}pyridine-3-carboxamide |
| 49 | (S)-5-bromo-N-{[1-(8-trifluoromethyl-1,4-benzodioxan-2-ylmethyl)-4-piperidyl]methyl}pyridine-3-carboxamide |
| 50 | (S)-N-{[1-(8-chloro-1,4-benzodioxan-2-ylmethyl)-4-piperidyl)methyl}-6-(1-pyrrolyl)pyridine-3-carboxamide |
| 51 | (S)-N{[1-8-chloro-1,4-benzodioxan-2-ylmethyl)-4-piperidyl]methyl}-2-(methylthio)pyridine-3-carboxamide |
| 52 | (S)-5-bromo-N-{[1-(8-chloro-1,4-benzodioxan-2-ylmethyl)-4-piperidyl]methyl}pyridine-3-carboxamide |

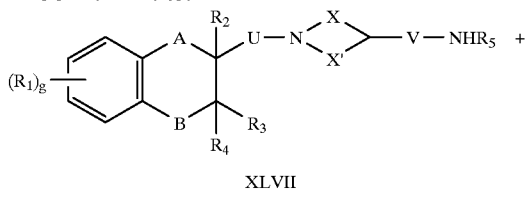

XLVII

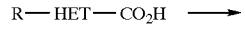

R—HET—CO$_2$H ⟶

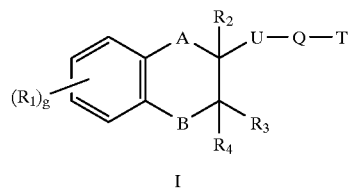

I 6 different compounds of formula XLVII (g is 1; A is O; B is O; U is methylene; X is ethylene; X' is ethylene; V is methylene; R$_5$ is H; and R$_1$ is 7-methyl, 7-bromo, 7-chloro, 7-fluoro, 8-trifluoromethyl, or 8-chloro) and 5 different compounds of formula R-HET-CO$_2$H (HET is 3-pyridinyl and R is H, 2-methyl, 6-(1-pyrrolyl), 2-methylthio or 5-bromo; were used as starting materials.

A compound of formula R-HET-CO$_2$H (0.1 mmol) was weighed into a 2 ml reaction vial. A compound of formula XLVII (0.1 mmol) was dissolved in dry dichloromethane (0.5 ml) and added to the vial. N,N'-diisopropylcarbodiimide (0.1 mmol) was then added and the mixture stirred under nitrogen at 20° C. for 5.5 hours. The solvent was removed by exposing the vial to reduced pressure in a vacuum dessicator for 20 minutes. Digol (1 ml) was added and stirring resumed until the reaction residue was redissolved/resuspended (0.1 M concentration). 20 μl of this material was added to Digol (1.98 ml) to give a 0.001 M solution which was tested for receptor binding affinity for 5HT$_{1A}$, α$_1$, and D$_2$ receptors.

EXAMPLE 53

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose are de-aggregated and blended. The mixture is filled into hard gelatin capsules, each capsule containing a unit dose of part of a unit dose of active compound.

b) Tablets

Tablets are prepared from the following ingredients.

|  | Parts by weight |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinylpyrrolidone in ethanol. The dry granulate is blended with the magnesium stearate and the rest of the starch. The mixture is then compressed in a tabletting machine to give tablets each containing a unit dose or a part of a unit dose of active compound.

c) Enteric coated tablets

Tablets are prepared by the method described in (b) above. The tablets are enteric coated in a conventional manner using a solution of 20% cellulose acetate phthalate and 3% diethyl phthalate in ethanol:dichloromethane (1:1).

d) Suppositories

In the preparation of suppositories, 100 parts by weight of active compound is incorporated in 1300 parts by weight of triglyceride suppository base and the mixture formed into suppositories each containing a therapeutically effective amount of active ingredient.

We claim:
1. Compounds of formula I

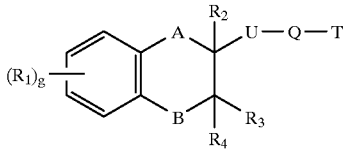

including pharmaceutically acceptable salts thereof in which
A is —O—;
B is —O—;
g is 0, 1, 2, 3 or 4;
$R_1$ represents a) halo; b) an alkyl group containing 1 to 3 carbon atoms optionally substituted by one or more halo; c) an alkoxy group containing 1 to 3 carbon atoms optionally substituted by one or more halo; d) an alkylthio group containing 1 to 3 carbon atoms optionally substituted by one or more halo; e) hydroxy; f) an acyloxy group containing 1 to 3 carbon atoms; g) hydroxymethyl: h) cyano; i) an alkanoyl group containing 1 to 6 carbon atoms; j) an alkoxycarbonyl group containing 2 to 6 carbon atoms; k) a carbamoyl group or carbamoylmethyl group each optionally N-substituted by one or two alkyl groups each containing 1 to 3 carbon atoms; l) a sulphamoyl or sulphamoylmethyl group each optionally N-substituted by one or two alkyl groups each containing 1 to 3 carbon atoms; m) an alkylsulphonyloxy group containing 1 to 3 carbon atoms optionally substituted by one or more halo; n) a furyl group; o) an amino group optionally substituted by one or two alkyl groups each containing 1 to 3 carbon atoms; or two adjacent $R_1$ groups together with the carbon atoms to which they are attached form a fused benzene ring, the substituents represented by $R_1$ being the same or different when g is 2, 3 or 4;
$R_2$ is H, an alkyl group containing 1 to 3 carbon atoms optionally substituted by one or more halo, or an alkoxy group containing 1 to 3 carbon atoms optionally substituted by one or more halo;
$R_3$ and $R_4$, which are the same or different, are H, or an alkyl group containing 1 to 3 carbon atoms optionally substituted by one or more halo;
U is an alkylene chain containing 1 to 3 carbon atoms, optionally substituted by one or more alkyl groups each containing 1 to 3 carbon atoms;
Q represents a divalent group of formula IIa, or IIc

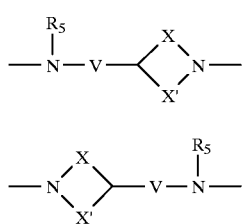

in which V is a bond or an alkylene chain containing 1 to 3 carbon atoms optionally substituted by one or more alkyl groups each containing 1 to 3 carbon atoms;
X is an alkylene chain containing 0 to 2 carbon atoms and X' is an alkylene chain containing 1 to 4 carbon atoms provided that the total number of carbon atoms in X and X' amounts to 3 or 4; $R_5$ is H or an alkyl group containing 1 to 3 carbon atoms; and
T represents the group CO.HET in which HET is 2-, 3- or 4-pyridyl, 2-, 4- or 5-pyrimidinyl, 2- or 3-thienyl, 2- or 3-furyl, 2-, 3- or 7-benzo[b]furanyl, 2,3-dihydro-7-benzo[b]furanyl, 2-, 3- or 7-benzo[b]thienyl, 2-, 3- or 4-piperidyl, 3-, 4- or 5-pyrazolyl, 4- or 5-triazolyl, 5-tetrazolyl, 2-, 3-, 4-, or 8-quinolinyl, 2- or 4-quinazolinyl, 3-, 4- or 5-isoxazolyl, 2-, 4- or 5-oxazolyl, 3-, 4- or 5-isothiazolyl or 2-, 4- or 5-thiazolyl each of which may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group containing 1 to 3 carbon atoms optionally substituted by one or more halo, e) hydroxy, f) an acyloxy group containing 1 to 3 carbon atoms, g) hydroxymethyl, h) cyano, i) an alkanoyl group containing 1 to 6 carbon atoms, j) an alkoxycarbonyl group containing 2 to 6 carbon atoms, k) a carbamoyl group or carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, m) an amino group optionally substituted by one or two alkyl groups each containing 1 to 5 carbon atoms, n) 1-pyrrolyl or o) 1-pyrrolidinyl or piperidino.

2. Compounds of formula I as claimed in claim 1 in which g is 0, 1 or 2; $R_1$ represents halo, an alkyl group containing 1 to 3 carbon atoms optionally substituted by one or more halo, an alkoxy group containing 1 to 3 carbon atoms, an alkylsulphonyloxy group containing 1 to 3 carbon atoms optionally substituted by one or more halo, or hydroxy; $R_2$ is H or an alkyl group containing 1 to 3 carbon atoms; $R_3$ and $R_4$, which are the same or different, are H or methyl; U is methylene; Q is a group of formula IIa or IIc; V is methylene; $R_5$ is H or methyl; X and X' are both ethylene; and HET is 2-, 3- or 4-pyridyl, 8-quinolinyl, or 2-thienyl each optionally substituted by one or more substituents selected from methyl, methoxy, trifluoromethyl, halo, methylthio, 1-pyridyl, or an amino group optionally substitued by one or two alkyl groups each containing 1 to 3 carbon atoms.

3. Compounds of formula I as claimed in claim 1 in which HET is 2-pyridyl, 3-pyridyl, 8-quinolinyl, or 2-thienyl each optionally substituted by an amino group, methyl, methoxy, 1-pyrrolyl, trifluoromethyl, methylthio or bromo.

4. Compounds of formula I as claimed in claim 3 in which HET is 2-pyridyl, or 3-pyridyl optionally substituted by an amino group.

5. Compounds of formula I as claimed in claim 1 selected from:
2-Amino-N-{[1-(7-chloro-1,4-benzodioxan-2-ylmethyl)-4-piperidyl]methyl}pyridine-3-carboxamide;
2-Amino-N-{[1-(8-chloro-1,4-benzodioxan-2-ylmethyl)-4-piperidyl]methyl}pyridine-3-carboxamide;
2-Amino-N-{[1-(8-fluoro-1,4-benzodioxan-2-ylmethyl)-4-piperidyl]methyl}pyridine-3-carboxamide;
2-Amino-N-{[1-(1,4-benzodioxan-2-ylmethyl)-4-piperidyl]methyl}pyridine-3-carboxamide;
2-Amino-N-{[1-(7-methyl-1,4-benzodioxan-2-ylmethyl)-4-piperidyl]methyl}pyridine-3-carboxamide;
N-{[1-(1,4-Benzodioxan-2-ylmethyl)-4-piperidyl]methyl}pyridine-2-carboxamide;

2-Amino-N-{[1-(7-methoxy-1,4-benzodioxan-2-ylmethyl)-4-piperidyl]methyl}pyridine-3-carboxamide;
N-{[1-(1,4-Benzodioxan-2-ylmethyl)-4-piperidyl]methyl}quinoline-8-carboxamide;
N-{[1-(8-Chloro-1,4-benzodioxan-2-ylmethyl)-4-piperidyl]methyl}-2-methylpyridine-3-carboxamide;
2-Amino-N{[1-(7-fluoro-1,4-benzodioxan-2-ylmethyl)-4-piperidyl]methyl}pyridine-3-carboxamide;
2-Amino-N-{[1-(8-methoxy-1,4-benzodioxan-2-ylmethyl)-4-piperidyl]methyl}pyridine-3-carboxamide;
N-{[1-(7-Chloro-1,4-benzodioxan-2-ylmethyl)-4-piperidyl]methyl}pyridine-2-carboxamide;
2-Amino-N-{[1-(8-methyl-1,4-benzodioxan-2-ylmethyl)-4-piperidyl]methyl}pyridine-3-carboxamide;
2-Amino-N-{[1-(7-chloro-1,4-benzodioxan-2-ylmethyl)-4-piperidyl]methyl}-6-methylpyridine-3-carboxamide;
3-Amino-N-{[1-(1,4-benzodioxan-2-ylmethyl)-4-piperidyl]methyl}-thiophene-2-carboxamide;
3-Amino-N-{[1-(7-chloro-1,4-benzodioxan-2-ylmethyl)-4-piperidyl]methyl}thiophene-2-carboxamide;
N-{[1-(7-Chloro-1,4-benzodioxan-2-ylmethyl)-4-piperidyl]methyl}-2-methylpyridine-3-carboxamide;
1-(2-Aminonicotinoyl)-4N-(7-chloro-1,4-benzodioxan-2-ylmethyl)aminomethylpiperidine;
2-Amino-N{[1-(8-trifluoromethyl-1,4-benzodioxan-2-ylmethyl)-4-piperidyl]methyl}pyridine-3-carboxamide;
2-Amino-N-{[1-(7-bromo-1,4-benzodioxan-2-ylmethyl)-4-piperidyl]methyl}pyridine-3-carboxamide;
N-{[1-(7-Chloro-1,4-benzodioxan-2-ylmethyl)-4-piperidyl]methyl}pyridine-3-carboxamide;
N-{[1-(7-Chloro-1,4-benzodioxan-2-ylmethyl)-4-piperidyl]methyl}quinoline-8-carboxamide;
N-{[1-(8-Chloro-1,4-benzodioxan-2-ylmethyl)-4-piperidyl]methyl}pyridine-3-carboxamide;
N-{[1-(7-Chloro-1,4-benzodioxan-2-ylmethyl)-4-piperidyl]methyl}-6-methylpyridine-2-carboxamide;
N-{[1-(7-Chloro-1,4-benzodioxan-2-ylmethyl)-4-piperidyl]methyl}-2-methoxypyridine-3-carboxamide;
2-Amino-N-{[1-(7,8-difluoro-1,4-benzodioxan-2-ylmethyl)-4-piperidyl]methyl}pyridine-3-carboxamide;
2-Amino-N-{[1-(8-trifluoromethanesulphonyloxy-1,4-benzodioxan-2-ylmethyl)-4-piperidyl]methyl}pyridine-3-carboxamide;
4-[N-(7-Chloro-1,4-benzodioxan-2-ylmethyl)aminomethyl]-1-(2-pyridylcarbonyl)-piperidine;
N-{[1-(7-Methyl-1,4-benzodioxan-2-ylmethyl)-4-piperidyl]methyl}pyridine-3-carboxamide;
2-Methyl-N-{[1-(7-methyl-1,4-benzodioxan-2-ylmethyl)-4-piperidyl]methyl}pyridine-3-carboxamide;
N-{[1-(7-Methyl-1,4-benzodioxan-2-ylmethyl)-4-piperidyl]methyl}-6-(1-pyrrolyl)pyridine-3-carboxamide;
N-{[1-(7-Methyl-1,4-benzodioxan-2-ylmethyl)-4-piperidyl]methyl}-2-(methylthio)pyridine-3-carboxamide;
5-Bromo- N-{[1-(7-methyl-1,4-benzodioxan-2-ylmethyl)-4-piperidyl]methyl}pyridine-3-carboxamide;
N-{[1-(7-Bromo-1,4-benzodioxan-2-ylmethyl)-4-piperidyl]methyl}pyridine-3-carboxamide;
N-{[1-(7-Bromo-1,4-benzodioxan-2-ylmethyl)-4-piperidyl]methyl}-2-methylpyridine-3-carboxamide;
N-{[1-(7-Bromo-1,4-benzodioxan-2-ylmethyl)-4-piperidyl]methyl}-6-(1-pyrrolyl)pyridine-3-carboxamide;
N-{[1-(7-Bromo-1,4-benzodioxan-2-ylmethyl)-4-piperidyl]methyl}-2-(methylthio)pyridine-3-carboxamide;
5-Bromo-N-{[1-(7-bromo-1,4-benzodioxan 2-ylmethyl)-4-piperidyl]methyl}pyridine-3-carboxamide;
N-{[1-(7-Chloro-1,4-benzodioxan-2-ylmethyl)-4-piperidyl]methyl}-6-(1-pyrrolyl)pyridine-3-carboxamide;
N-{[1-(7-Chloro-1,4-benzodioxan-2-ylmethyl)-4-piperidyl]methyl}-2-(methylthio)pyridine-3-carboxamide;
5-Bromo- N-{[1-(7-chloro-1,4-benzodioxan-2-ylmethyl)-4-piperidyl]methyl}pyridine-3-carboxamide;
N-{[1-(7-Fluoro-1,4-benzodioxan-2-ylmethyl)-4-piperidyl]methyl}pyridine-3-carboxamide;
N-{[1-(7-Fluoro-1,4-benzodioxan-2-ylmethyl)-4-piperidyl]methyl}-2-(methylthio)pyridine-3-carboxamide;
N-{[1-(8-Trifluoromethyl-1,4-benzodioxan-2-ylmethyl)-4-piperidyl]methyl}pyridine-3-carboxamide;
2-Methyl-N-{[1-(8-trifluoromethyl-1,4-benzodioxan-2-ylmethyl)-4-piperidyl]methyl}pyridine-3-carboxamide;
6-(1-Pyrrolyl)-N-{[1-(8-trifluoromethyl-1,4-benzodioxan-2-ylmethyl)-4-piperidyl]methyl}pyridine-3-carboxamide;
2-(Methylthio)-N-{[1-(8-trifluoromethyl-1,4-benzodioxan-2-ylmethyl)-4-piperidyl]methyl}pyridine-3-carboxamide;
5-Bromo-N-{[1-(8-trifluoromethyl-1,4-benzodioxan-2-ylmethyl)-4-piperidyl]methyl}pyridine-3-carboxamide;
N-{[1-(8-Chloro-1,4-benzodioxan-2-ylmethyl)-4-piperidyl]methyl}-6-(1-pyrrolyl)pyridine-3-carboxamide;
N-{[1-(8-Chloro-1,4-benzodioxan-2-ylmethyl)-4-piperidyl]methyl}-2-(methylthio)pyridine-3-carboxamide;
5-Bromo-N-{[1-(8-chloro-1,4-benzodioxan-2-ylmethyl)-4-piperidyl]methyl}pyridine-3-carboxamide;

and pharmaceutically acceptable salts thereof in the form of individual enantiomers, racemates, or mixtures of these enantiomers.

6. A composition comprising a therapeutically effective amount of a compound of formula I as claimed in claim 1 or a salt thereof together with a pharmaceutically acceptable diluent or carrier.

7. A method of treating depression, anxiety, psychoses, tardive dyskinesia, Parkinson's disease, hypertension, Tourette's syndrome, obsessive-compulsive behaviour, panic attacks, social phobias, cardiovascular and cerebrovascular disorders, stress or prostatic hypertrophy in human beings which comprises the administration of a therapeutically effective amount of a compound of formula I as defined in claim 1 to a mammal, particularly a human being, in need thereof.

8. A method, as claimed in claim 7, for the treatment of schizophrenia.

9. A process for the preparation of a compound of formula I as claimed in claim 1 in which Q is a group of formula IIa comprising the reaction of compound of formula XXXVI

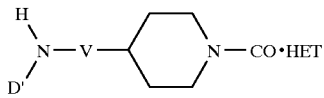    XXXVI in which D' is H, with a compound of formula VII

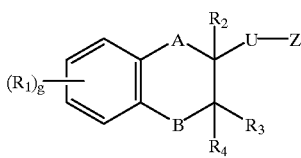    VII in which Z is toluene-4-sulphonyloxy, optionally in the presence of a base, and optionally in a solvent.

10. A process for the preparation of compound of formula I as claimed in claim 1 in which Q is a group of formula IIc comprising the reaction of a compound of formula XLV

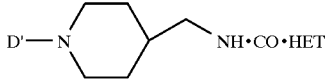    XLV in which D' is H, with a compound of formula VII

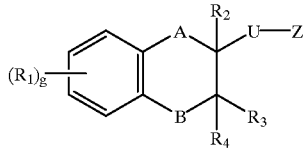    VII in which Z is toluene-4-sulphonyloxy, optionally in the presence of a base, and optionally in a solvent.

11. A process for the preparation of compound of formula I as claimed in claim I in which Q is a group of formula IIc comprising the reaction of a compound of formula XLVII

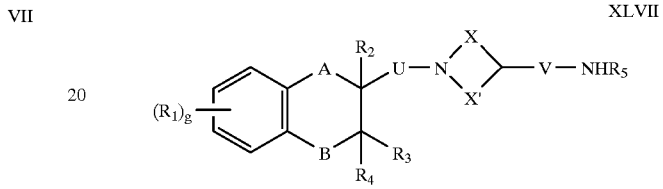    XLVII with a) a compound of formula XXXIX

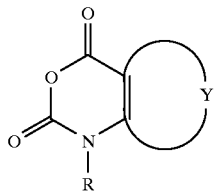    XXXIX in which Y completes a heteroaromatic ring and R is H or alkyl, which is pyrido(2,3-d)(1,3)oxazine-2,4(1H)-dione optionally in the presence of a solvent,; or (b) with an acylating compound of formula X"-CO.HET in which X" is halo, alkoxy, hydroxy or alkoxycarbonyloxy, in the presence of a base, or an amide bond forming agent, in a suitable solvent.

* * * * *

UNITED STATES PATENT AND TRADEMARK OFFICE
CERTIFICATE OF CORRECTION

PATENT NO.: 5,935,973

DATED: August 10, 1999

INVENTOR(S): BIRCH et al.

It is certified that error appears in the above-identified patent and that said Letters Patent is hereby corrected as shown below:

Col. 52, claim 2, line 44, "1-pyridyl" should be --1-pyrrolyl--.

Col. 53, claim 5, line 29, after "N" insert a dash -- - --.

Signed and Sealed this

Eleventh Day of January, 2000

Attest:

Q. TODD DICKINSON

*Attesting Officer*  Acting Commissioner of Patents and Trademarks